(12) United States Patent
Lecron et al.

(10) Patent No.: US 7,901,669 B2
(45) Date of Patent: Mar. 8, 2011

(54) COMPOSITIONS FOR ENHANCING KERATINOCYTE MIGRATION AND EPIDERMAL REPAIR VIA A RECEPTOR CONTAINING OSMRβ AS A SUBUNIT, AND APPLICATIONS THEREOF

(75) Inventors: Jean-Claude Lecron, Bonnes (FR); Hughes Gascan, Angers (FR); Franck Morel, Savigny l'Evescault (FR); Sylvie Chevalier, Angers (FR); François-Xavier Bernard, Saint Maurice la Clouere (FR); Katia Boniface, Mountain View, CA (US); Caroline Diveu, Palo Alto, CA (US)

(73) Assignees: Universite d'Angers, Angers (FR); Universite de Poitiers, Poitiers Cedes (FR); Bioalternatives SAS, Gencay (FR)

( * ) Notice: Subject to any disclaimer, the term of this patent is extended or adjusted under 35 U.S.C. 154(b) by 197 days.

(21) Appl. No.: 11/721,888

(22) PCT Filed: Dec. 15, 2005

(86) PCT No.: PCT/EP2005/014199
§ 371 (c)(1),
(2), (4) Date: Feb. 4, 2008

(87) PCT Pub. No.: WO2006/063865
PCT Pub. Date: Jun. 22, 2006

(65) Prior Publication Data
US 2009/0104146 A1   Apr. 23, 2009

(30) Foreign Application Priority Data
Dec. 15, 2004 (EP) .................................... 04293004

(51) Int. Cl.
*A61K 38/19* (2006.01)
*A61K 38/20* (2006.01)
(52) U.S. Cl. ..................... 424/85.1; 424/85.2; 514/18.6; 514/21.2
(58) Field of Classification Search ........................ None
See application file for complete search history.

(56) References Cited

U.S. PATENT DOCUMENTS

| 5,744,442 A | 4/1998 | Richards et al. |
| 5,874,536 A | 2/1999 | Linsley et al. |

FOREIGN PATENT DOCUMENTS

| WO | WO 02/33083 | 4/2002 |

OTHER PUBLICATIONS

International Search Report and Written Opinion mailed Jul. 3, 2006 for PCT/EP2005/014199 (Filed Dec. 15, 2005).

*Primary Examiner* — Prema Mertz
(74) *Attorney, Agent, or Firm* — Alston & Bird LLP

(57) ABSTRACT

The present invention relates to the field of epidermal repair. More particularly, the invention concerns the use of a molecule able to activate a heteromeric receptor comprising OSMRβ as a subunit, for the preparation of a composition for activating in vitro and/or in vivo keratinocyte migration and/or the expression of anti-microbial peptides by the keratinocytes. In particular, the invention concerns the use of OSM and/or IL-17 and/or TNFα and/or IL-31, or agonists thereof, for the preparation of cosmetic or dermatologic compositions.

5 Claims, 11 Drawing Sheets

A 
B

SEQUENCE LISTING

```
<160> NUMBER OF SEQ ID NOS: 32

<210> SEQ ID NO 1
<211> LENGTH: 20
<212> TYPE: DNA
<213> ORGANISM: Artificial
<220> FEATURE:
<223> OTHER INFORMATION: forward primer for reverse transcription
      of OSMR

<400> SEQUENCE: 1
cctgcctacc tgaaaaccag                                              20

<210> SEQ ID NO 2
<211> LENGTH: 20
<212> TYPE: DNA
<213> ORGANISM: Artificial
<220> FEATURE:
<223> OTHER INFORMATION: reverse primer for reverse transcription
      of OSMR

<400> SEQUENCE: 2
acattggtgc cttcttccac                                              20

<210> SEQ ID NO 3
<211> LENGTH: 22
<212> TYPE: DNA
<213> ORGANISM: Artificial
<220> FEATURE:
<223> OTHER INFORMATION: forward primer for reverse transcription
      of gp130

<400> SEQUENCE: 3
gggcaatatg actctttgaa gg                                           22

<210> SEQ ID NO 4
<211> LENGTH: 22
<212> TYPE: DNA
<213> ORGANISM: Artificial
<220> FEATURE:
<223> OTHER INFORMATION: reverse primer for reverse transcription
      of gp130

<400> SEQUENCE: 4
ttcctgttga tgttcagaat gg                                           22

<210> SEQ ID NO 5
<211> LENGTH: 20
<212> TYPE: DNA
<213> ORGANISM: Artificial
<220> FEATURE:
<223> OTHER INFORMATION: forward primer for reverse transcription
      of LIFR

<400> SEQUENCE: 5
cagtacaaga gcagcggaat                                              20
```

```
<210> SEQ ID NO 6
<211> LENGTH: 20
<212> TYPE: DNA
<213> ORGANISM: Artificial
<220> FEATURE:
<223> OTHER INFORMATION: reverse primer for reverse transcription
      of LIFR

<400> SEQUENCE: 6
ccagtccata aggcatggtt                                              20

<210> SEQ ID NO 7
<211> LENGTH: 20
<212> TYPE: DNA
<213> ORGANISM: Artificial
<220> FEATURE:
<223> OTHER INFORMATION: forward primer for reverse transcription
      of GAPDH

<400> SEQUENCE: 7
accacagtcc atgccatcac                                              20

<210> SEQ ID NO 8
<211> LENGTH: 20
<212> TYPE: DNA
<213> ORGANISM: Artificial
<220> FEATURE:
<223> OTHER INFORMATION: reverse primer for reverse transcription
      of GAPDH

<400> SEQUENCE: 8
tccaccaccc tgttgctgta                                              20

<210> SEQ ID NO 9
<211> LENGTH: 28
<212> TYPE: DNA
<213> ORGANISM: Artificial
<220> FEATURE:
<223> OTHER INFORMATION: forward primer for Q-RT-PCR of S100A7

<400> SEQUENCE: 9
gcatgatcga catgtttcac aaatacac                                     28

<210> SEQ ID NO 10
<211> LENGTH: 23
<212> TYPE: DNA
<213> ORGANISM: Artificial
<220> FEATURE:
<223> OTHER INFORMATION: reverse primer for Q-RT-PCR of S100A7

<400> SEQUENCE: 10
tggtagtctg tggctatgtc tcc                                          23

<210> SEQ ID NO 11
<211> LENGTH: 26
<212> TYPE: DNA
<213> ORGANISM: Artificial
<220> FEATURE:
<223> OTHER INFORMATION: forward primer for Q-RT-PCR of S100A9

<400> SEQUENCE: 11
gctcctcggc tttgacagag tgcaag                                       26

<210> SEQ ID NO 12
<211> LENGTH: 30
<212> TYPE: DNA
<213> ORGANISM: Artificial
<220> FEATURE:
```

```
<223> OTHER INFORMATION: reverse primer for Q-RT-PCR of S100A9

<400> SEQUENCE: 12
gcatttgtgt ccaggtcctc catgatgtgt                                    30

<210> SEQ ID NO 13
<211> LENGTH: 22
<212> TYPE: DNA
<213> ORGANISM: Artificial
<220> FEATURE:
<223> OTHER INFORMATION: forward primer for Q-RT-PCR of hBD2/4

<400> SEQUENCE: 13
gccatcagcc atgagggtct tg                                            22

<210> SEQ ID NO 14
<211> LENGTH: 21
<212> TYPE: DNA
<213> ORGANISM: Artificial
<220> FEATURE:
<223> OTHER INFORMATION: reverse primer for Q-RT-PCR of hBD2/4

<400> SEQUENCE: 14
aatccgcatc agccacagca g                                             21

<210> SEQ ID NO 15
<211> LENGTH: 20
<212> TYPE: DNA
<213> ORGANISM: Artificial
<220> FEATURE:
<223> OTHER INFORMATION: forward primer for Q-RT-PCR of KRT10

<400> SEQUENCE: 15
gcccgacggt agagttcttt                                               20

<210> SEQ ID NO 16
<211> LENGTH: 21
<212> TYPE: DNA
<213> ORGANISM: Artificial
<220> FEATURE:
<223> OTHER INFORMATION: reverse primer for Q-RT-PCR of KRT10

<400> SEQUENCE: 16
cagaaaccac aaaacacctt g                                             21

<210> SEQ ID NO 17
<211> LENGTH: 20
<212> TYPE: DNA
<213> ORGANISM: Artificial
<220> FEATURE:
<223> OTHER INFORMATION: forward primer for Q-RT-PCR of OSM

<400> SEQUENCE: 17
tcagtctggt ccttgcactc                                               20

<210> SEQ ID NO 18
<211> LENGTH: 20
<212> TYPE: DNA
<213> ORGANISM: Artificial
<220> FEATURE:
<223> OTHER INFORMATION: reverse primer for Q-RT-PCR of OSM

<400> SEQUENCE: 18
ctgcagtgct ctctcagttt                                               20

<210> SEQ ID NO 19
```

```
<211> LENGTH: 19
<212> TYPE: DNA
<213> ORGANISM: Artificial
<220> FEATURE:
<223> OTHER INFORMATION: forward primer for Q-RT-PCR of GAPDH

<400> SEQUENCE: 19
gaaggtgaag gtcggagtc                                                 19

<210> SEQ ID NO 20
<211> LENGTH: 20
<212> TYPE: DNA
<213> ORGANISM: Artificial
<220> FEATURE:
<223> OTHER INFORMATION: reverse primer for Q-RT-PCR of GAPDH

<400> SEQUENCE: 20
gaagatggtg atgggatttc                                                20

<210> SEQ ID NO 21
<211> LENGTH: 22
<212> TYPE: DNA
<213> ORGANISM: Artificial
<220> FEATURE:
<223> OTHER INFORMATION: forward primer for Q-RT-PCR of murine
      S100A8

<400> SEQUENCE: 21
tccaatatac aaggaaatca cc                                             22

<210> SEQ ID NO 22
<211> LENGTH: 18
<212> TYPE: DNA
<213> ORGANISM: Artificial
<220> FEATURE:
<223> OTHER INFORMATION: reverse primer for Q-RT-PCR of murine
      S100A8

<400> SEQUENCE: 22
tttatcacca tcgcaagg                                                  18

<210> SEQ ID NO 23
<211> LENGTH: 20
<212> TYPE: DNA
<213> ORGANISM: Artificial
<220> FEATURE:
<223> OTHER INFORMATION: forward primer for Q-RT-PCR of murine
      S100A9

<400> SEQUENCE: 23
gaaggaattc agacaaatgg                                                20

<210> SEQ ID NO 24
<211> LENGTH: 18
<212> TYPE: DNA
<213> ORGANISM: Artificial
<220> FEATURE:
<223> OTHER INFORMATION: reverse primer for Q-RT-PCR of murine
      S100A9

<400> SEQUENCE: 24
atcaactttg ccatcagc                                                  18

<210> SEQ ID NO 25
<211> LENGTH: 19
<212> TYPE: DNA
<213> ORGANISM: Artificial
<220> FEATURE:
```

```
<223> OTHER INFORMATION: forward primer for Q-RT-PCR of murine
      MIP-1 beta

<400> SEQUENCE: 25
cctctctctc ctcttgctc                                                        19

<210> SEQ ID NO 26
<211> LENGTH: 20
<212> TYPE: DNA
<213> ORGANISM: Artificial
<220> FEATURE:
<223> OTHER INFORMATION: reverse primer for Q-RT-PCR of murine
      MIP-1 beta

<400> SEQUENCE: 26
agatctgtct gcctcttttg                                                       20

<210> SEQ ID NO 27
<211> LENGTH: 18
<212> TYPE: DNA
<213> ORGANISM: Artificial
<220> FEATURE:
<223> OTHER INFORMATION: forward primer for Q-RT-PCR of murine MDC

<400> SEQUENCE: 27
tgctgccagg actacatc                                                         18

<210> SEQ ID NO 28
<211> LENGTH: 19
<212> TYPE: DNA
<213> ORGANISM: Artificial
<220> FEATURE:
<223> OTHER INFORMATION: reverse primer for Q-RT-PCR of murine MDC

<400> SEQUENCE: 28
tagcttcttc acccagacc                                                        19

<210> SEQ ID NO 29
<211> LENGTH: 20
<212> TYPE: DNA
<213> ORGANISM: Artificial
<220> FEATURE:
<223> OTHER INFORMATION: forward primer for Q-RT-PCR of murine TARC

<400> SEQUENCE: 29
cattcctatc aggaagttgg                                                       20

<210> SEQ ID NO 30
<211> LENGTH: 19
<212> TYPE: DNA
<213> ORGANISM: Artificial
<220> FEATURE:
<223> OTHER INFORMATION: reverse primer for Q-RT-PCR of murine TARC

<400> SEQUENCE: 30
cttgggtttt tcaccaatc                                                        19

<210> SEQ ID NO 31
<211> LENGTH: 19
<212> TYPE: DNA
<213> ORGANISM: Artificial
<220> FEATURE:
<223> OTHER INFORMATION: forward primer for Q-RT-PCR of murine GAPDH

<400> SEQUENCE: 31
atcaagaagg tggtgaagc                                                        19
```

-continued

```
<210> SEQ ID NO 32
<211> LENGTH: 20
<212> TYPE: DNA
<213> ORGANISM: Artificial
<220> FEATURE:
<223> OTHER INFORMATION: reverse primer for Q-RT-PCR of murine GAPDH

<400> SEQUENCE: 32
gccgtattca ttgtcatacc                                                    20
```

US 7,901,669 B2

COMPOSITIONS FOR ENHANCING KERATINOCYTE MIGRATION AND EPIDERMAL REPAIR VIA A RECEPTOR CONTAINING OSMRβ AS A SUBUNIT, AND APPLICATIONS THEREOF

CROSS REFERENCE TO RELATED APPLICATIONS

This application is a national stage application filed under 35 USC 371 of International Application No. PCT/EP2005/014199, filed Dec. 15, 2005, which claims priority from European patent application 04293004.0 filed Dec. 15, 2004.

FIELD AND BACKGROUND OF THE INVENTION

The present invention relates to the field of epidermal repair. More particularly, the invention concerns the use of a molecule able to activate a heteromeric receptor comprising OSMRβ as a subunit, for the preparation of a composition for enhancing in vitro and/or in vivo keratinocyte migration.

The skin is a large and complex tissue providing a protective interface between an organism and its environment. Epidermis forms its external surface, and is mainly constituted of multiple layers of specialized epithelial cells named keratinocytes. Skin can be injured by many different causes, including micro-organisms, chemicals, behaviours, physical injury, ageing, U.V. irradiation, cancer, autoimmune or inflammatory diseases.

Epidermis homeostasis is regulated by a balance between differentiation and proliferation of keratinocytes, differentiating from the basal to the cornified layers of the skin. In response to epidermal stress or in some skin diseases, this equilibrium is broken. Keratinocytes become able to differentially respond to soluble mediators such as Epidermal Growth Factor (EGF) family members, and to additional growth factors and cytokines (FGFs, IGF-1, PDGF, HGF, TGFβ family members, GM-CSF, TSLP, IL-1, TNF-α). These modulators are produced by the keratinocytes themselves, the skin fibroblasts, the Langerhans cells or by immune infiltrating cells such as T lymphocytes. In response, the keratinocytes release additional signaling molecules, modulate the expression level of cell surface receptors, modify their cytoskeleton morphology, and modulate their migration, differentiation and proliferation capacities. These changes are associated with an inflammatory response, leading to either wound healing or to a chronic disease.

The cytokines of the IL-6 family are multifunctional proteins regulating cell growth and differentiation in a large number of biological systems, such as immunity, hematopoiesis, neural development, reproduction, bone modeling and inflammatory processes. This cytokine family encompasses nine different members: IL-6, IL-11, IL-27, leukemia inhibitory factor (LIF), cardiotrophin-1, cardiotrophin-like factor, ciliary neurotrophic factor, neuropoietin, and oncostatin M (OSM). The activities of theses cytokines are mediated through ligand-induced oligomerization of a dimeric or trimeric receptor complex. The IL-6 family of cytokines shares the gp130 receptor subunit in the formation of their respective heteromeric receptors (Taga and Kishimoto 1997). A recently described cytokine, named IL-31, has been classified by Dillon et al as a novel member of the gp130-IL6 family, because its receptor is a heterodimer comprising gp130-like type I cytokine receptor (GPL) and an OSMR subunit (Dillon, Sprecher et al. 2004).

Different publications have reported that some members of the IL-6 family may be implicated in certain skin diseases and wound healing processes. IL-6, IL-11, LIF and OSM have been found to be increased in psoriatic lesions (Bonifati, Mussi et al. 1998), and IL-6 and LIF are produced by purified keratinocytes (Paglia, Kondo et al. 1996; Sugawara, Gallucci et al. 2001). An impaired wound healing process has been reported in IL-6 and STAT3 deficient mice (Sano, Itami et al. 1999; Gallucci, Simeonova et al. 2000). However, further studies on cultured keratinocytes isolated from IL-6 deficient mice showed that the action of IL-6 on keratinocyte migration is mediated by dermal fibroblasts. Indeed, IL-6 alone did not significantly modulate the proliferation or migration of said IL-6-deficient keratinocytes, whereas IL-6 significantly induced their migration when co-cultured with dermal fibroblasts (Gallucci, Sloan et al. 2004).

OSM is secreted from activated T cells, monocytes stimulated by cytokines and from dendritic cells. OSM is a pro-inflammatory mediator, which strongly triggers protein synthesis in hepatocytes (Benigni, Fantuzzi et al. 1996). In humans, OSM and LIF display overlapping biological functions in a number of tissues by increasing growth regulation, differentiation, gene expression, cell survival. OSM is also known to elicit some unique biological functions, not shared with LIF, such as growth inhibition of some tumor cell lines or stimulation of AIDS-associated Kaposi's sarcoma cells. These shared and specific functions of OSM are explained by the existence of two types of OSM receptor complexes. Beside the common LIF/OSM receptor complex made of gp130/LIFRβ subunits, OSM is also able to specifically recognize a type II receptor associating gp130 with OSMRβ (also referred to as "OSMR" or "OSM-R"), which is expressed by endothelial cells, hepatic cells, lung cells, fibroblasts, hematopoietic cells and by some tumor cell lines. The subsequent signaling cascade involves activation of the Janus kinase (JAK 1, JAK 2, Tyk 2), followed by an activation of the Signal Transducer and Activator of Transcription (STAT1, STAT3) and of the Map kinase pathways.

In addition to its anti-neoplastic activity and its role in the pro-inflammatory response (Wahl and Wallace 2001); Shoyab et al, U.S. Pat. No. 5,451,506; Richards et al., U.S. Pat. No. 5,744,442), OSM has been described as stimulating the growth of dermal fibroblasts via a MAP kinase-dependent pathway, thereby promoting dermal wound healing (Ihn and Tamaki 2000).

Other cytokines are also known to have an effect on dermis. For example, Dillon et al (supra) suggest that overexpression of IL-31 may be involved in promoting the dermatitis and epithelial responses that characterize allergic and non-allergic diseases. These authors do not suggest to use IL-31 for promoting skin repair.

When skin is injured, its complete repair implies that both the dermis and the epidermis are repaired. Healing of epidermis and dermis, which comprise different cell-types, involve different mechanisms.

Currently, treatments for improving skin healing mainly target the dermis. However, epidermis reconstitution is necessary for a complete recovering. In some cases, for example in the case of large burns, ulcers or bedscores, physiological epidermal healing processes are not efficient enough for restoring the protecting function of skin. In such cases, it is necessary to rapidly cover the damaged area, to avoid infections and possibly dehydration. It is also necessary to stimulate epidermis regeneration. In the case of severe burns on less than half of the body surface, skin auto-graft is performed after excision of the burnt skin. To that aim, sane skin is taken from the patient and mechanically treated for increasing its surface. This "wick-skin" is then grafted on the lesions. When the burnt surface is too large (more than half of the body surface), this process is not feasible. It is then necessary to temporarily cover the wounds to avoid dehydration and infection. This is currently performed with either skin from cadavers, or with skin substitutes such as acellular dressings like tulle gras, possibly incorporating growth factors for improving wound healing. Examples of such skin substitutes are described in U.S. Pat. No. 6,132,759 or in WO 01/41820. In parallel, skin cells from the patient are expanded in vitro, in order to obtain epithelial layers that are then grafted. One to 2 m² can be obtained in 3 weeks, from a few cm² of sane skin. However, these techniques are long, costly, and need a heavy infrastructure to be successfully performed. Hence it is clear that there exists a real need for novel dermatological approaches for improving epidermal repair. Enhancing centripetal migration of the keratinocytes would clearly accelerate/enable healing and re-epithelialization. Acting on the keratinocytes' differentiation differentiation and migration is also necessary for treating specific diseases such as bullous epidermolysis. The phrase "bullous emolysis" designates a number of dermatitis of different origins (such as bleds, burns, autoimmune diseases, . . . ), leading to a detachment of the epidermis and liquid accumulation between dermis and epidermis. A particular example of bullous epidermolysis is bullous phemphigoid.

Improving epidermal repair is also important in the cosmetic field, where no efficient compositions exist for improving the aspect of scars, originating either from recent small wounds or from old cuts, spots, stretch marks and the like.

In this context, the inventors found that several cytokines, in particular OSM and IL-31, can enhance the migration of keratinocytes. Interestingly, these two cytokines bind to different heteromeric receptors, that both comprise OSMRβ as a subunit. The inventors have shown that normal human epidermal keratinocytes express gp130, GPL and OSMRβ.

As disclosed in the experimental examples below, OSM recruits the STAT3 signaling pathways, as well as the MAP kinase pathways in human epidermal keratinocytes. OSM up-regulates the expression of pro-inflammatory genes in these cells, including chemokines, defensin and the psoriasin. OSM also increases the thickness of reconstituted human epidermis and down-regulates a set of differentiation antigens. Interestingly, other cytokines, especially IL-17 and TNFα, act synergistically with OSM and potentiate its effects.

Experiments conducted by the inventors also revealed that IL-31 can mediate keratinocyte migration. The inventors however observed, in glioblastoma and melanoma tumor cells, that the action of IL-31 depends on the type of GPL subunit involved with OSMRβ in the formation of the heteromeric receptor. In particular, they noticed that a short form of GPL receptor exerts a profound inhibitory effect on the signaling of IL-31 and behaves as a dominant negative receptor.

Taken together, these results indicate that OSM and IL-31 play important roles in wound healing and other processes involving keratinocyte migration. These effects require the signal transduction involving the OSMRβ subunit in heteromeric receptors.

SUMMARY OF THE INVENTION

A first object of the present invention is hence the use of at least one activator of a heteromeric receptor having OSMRβ as a subunit, for the preparation of a composition for improving epidermal repair.

Examples of such activators are the ligands of the heteromeric receptors comprising the OSMRβ subunit, as well as agonists thereof. Preferred activators according to the invention are cytokines, in particular oncostatin M (OSM) and interleukin 31 (IL-31), as well as agonists thereof. In what follows, "OSM" and "IL-31" will be used to designate the cytokines as such, as well as their respective agonists. Other examples of activators according to the invention are molecules which upregulate the expression of receptor subunits that are able to form a heteromeric receptor with OSMRβ.

IL-17 and TNFα, which potentiate the action of OSM, as well as gamma interferon (IFN-γ), which potentiates the effect of IL-31, can also be considered as activators according to the present invention, and can advantageously be used in combination with OSM or IL-31, respectively, in order to increase their effect, thereby enabling the use of lower concentrations in the compositions according to the invention. Of course, these cytokines can be replaced by agonists thereof. Mutated cytokines, native or mutated peptides different from a cytokine, and non-peptidic synthetic or natural molecules can thus be used as activators according to the invention.

In a preferred embodiment of the invention, OSM, IL-17 and TNFα are used for the preparation of a composition for improving epidermal repair.

Compositions obtained according to the invention can be used for promoting keratinocyte migration, or for promoting epidermal healing. These compositions will advantageously be used for stimulating centripetal migration of keratinocytes in case of large wounds. They can also be used for preventing, attenuating or treating bullous epidermolysis. Indeed, depending on its origin and stage, bullous epidermolysis can be treated either by administering molecules enhancing keratinocyte migration, or, to the contrary, anti-inflammatory molecules. The physician will know, depending on the context, when a treatment with OSM, IL-31 and/or their agonists and potentiators, can be beneficial for a patient suffering from bullous epidermolysis.

The compositions according to the invention can also be used for increasing epidermal thickness, either in vivo, for example by topic administration, or in vitro, to increase the quality and/or quantity of (human) reconstituted epidermis, for example to accelerate the production of epithelial layers for patients in need of a graft.

According to specific embodiments of the present invention, an activator of a heteromeric receptor having OSMRβ as a subunit, or a combination of molecules activating said receptor, is used for the preparation of a composition for preventing and/or attenuating chaps on hands, lips, face or body, or for preventing and/or attenuating stretch marks. Other applications of the compositions obtained according to the invention are the improvement of the aspect and comfort of scars, and/or the improvement of the aspect and comfort of epidermal wounds during their healing. According to this aspect of the invention, the wounds can be of any origin. They include those resulting from trauma such as cuts, burns, abrasions and the like, those resulting from surgical procedures such as surgical incisions and skin grafting, as well as those resulting from disorders and diseases like acne, atopic dermatitis, eczema, professional dermatitis, seborrheic dermatitis, rosacea, erythema, eschar, diabetes (feet), keratosis, squama, ulcers, ichtyosis, bullous epidermolysis, malum perforan pedis, wart, leprae infection, etc. Of course, in the case of wounds resulting from inflammatory diseases, or from diseases related to keratinocytes hyperproliferation, the physician will control that the disease is treated before the composition according to the invention is administered.

The compositions prepared according to the invention are preferably formulated for topic administration. They can for example be in the form of a cream, lotion, ointment, or dressing.

Particular cosmetic and/or dermatological compositions according to the invention comprise OSM or IL-31.

The invention also pertains to the use of at least two cytokines as above-described, for the preparation of dermatological and/or cosmetic compositions. These at least two cytokines can be either mixed in the same composition, or provided in a kit of parts. According to this aspect of the invention, a preferred kit of parts or composition comprises OSM and at least one cytokine selected amongst IL-17, TNFα and agonist(s) of these cytokines. A preferred cosmetic and/or dermatological composition according to the invention comprises OSM, IL-17 and TNFα. In another particular embodiment of the composition according to the invention, said composition comprises IL-31 and IFN-γ, and/or OSM.

In the compositions according to the invention comprising OSM, OSM is preferably in a concentration of 0.1 to 100 ng/ml, more preferably from 1 to 20 ng/ml. Its concentration can be lowered in the presence of IL-17 and/or TNFα, down to 0.01 ng/ml. In such complex compositions, the concentrations of OSM and/or IL-17 and/or TNFα are preferably from 0.01 ng/ml to 10 ng/ml, more preferably from 0.1 to 2 ng/ml. In the compositions comprising IL-31, this latter is preferably in a concentration of 1 to 500 ng/ml, more preferably from 10 to 100 ng/ml.

As mentioned above, it is possible to increase the quality and/or quantity of (human) reconstituted epidermis, by adding at least one activator of a heteromeric receptor having OSMRβ as a subunit to cultured keratinocytes. The invention hence also concerns a method of preparing a reconstituted human epidermis, comprising a step of adding at least one activator as described above, to keratinocytes in culture. For example, this method can be performed by adding OSM and/or IL-17 and/or TNFα to the culture medium of said keratinocytes, at concentrations preferably ranging 0.01 to 10 ng/ml for each cytokine.

BRIEF DESCRIPTION OF THE DRAWINGS

The invention is further illustrated by the following figures and examples:

FIGURES LEGENDS

Figure 1:
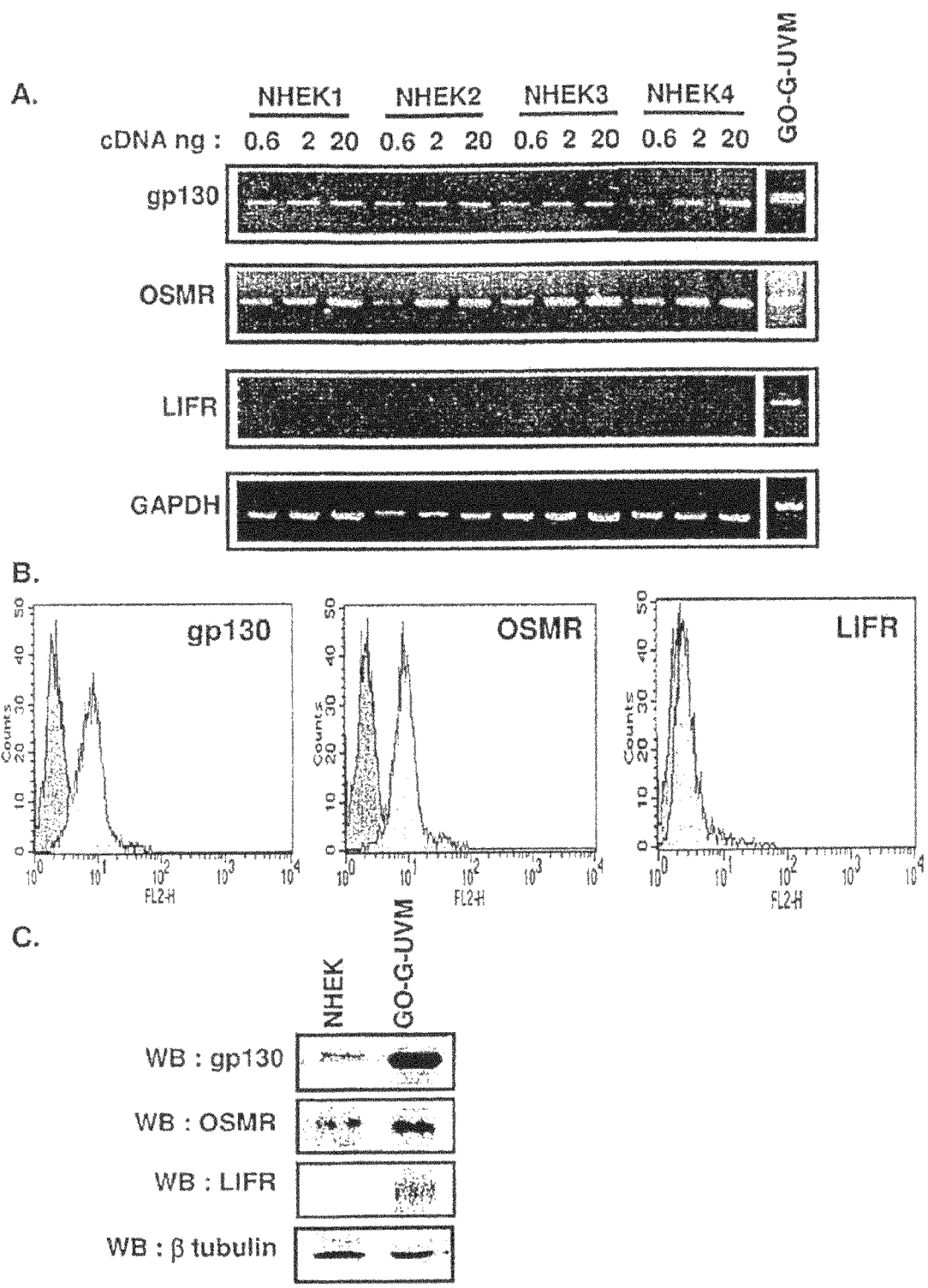

FIG. 1 shows the expression of OSM receptor by NHEK.

(A) Total RNA was extracted from NHEK of 4 independent donors. RT-PCR was performed with specific primers for OSMR, gp130, LIFR and GAPDH genes. Serial dilutions of cDNA were amplified to have a semi-quantitative analysis of transcripts expression level. PCR products were analysed by agarose gel electrophoresis. (B) Immunolabelling of cell surface NHEK and flux cytometry analysis. Gp130 and OSMR are clearly detected on the cell, but not the LIFR. (C) Twenty μg of cell lysate from NHEK and the glioblastoma cell line GO-G-UVM were separated by SDS-PAGE (10%) and transferred to nitrocellulose membrane. Ponceau red staining was used to control loading homogeneity. Detection of gp130, OSMR, LIFR and tubulin bands were assessed by Western blot. The results are representative of 3 independent experiments.

Figure 2:
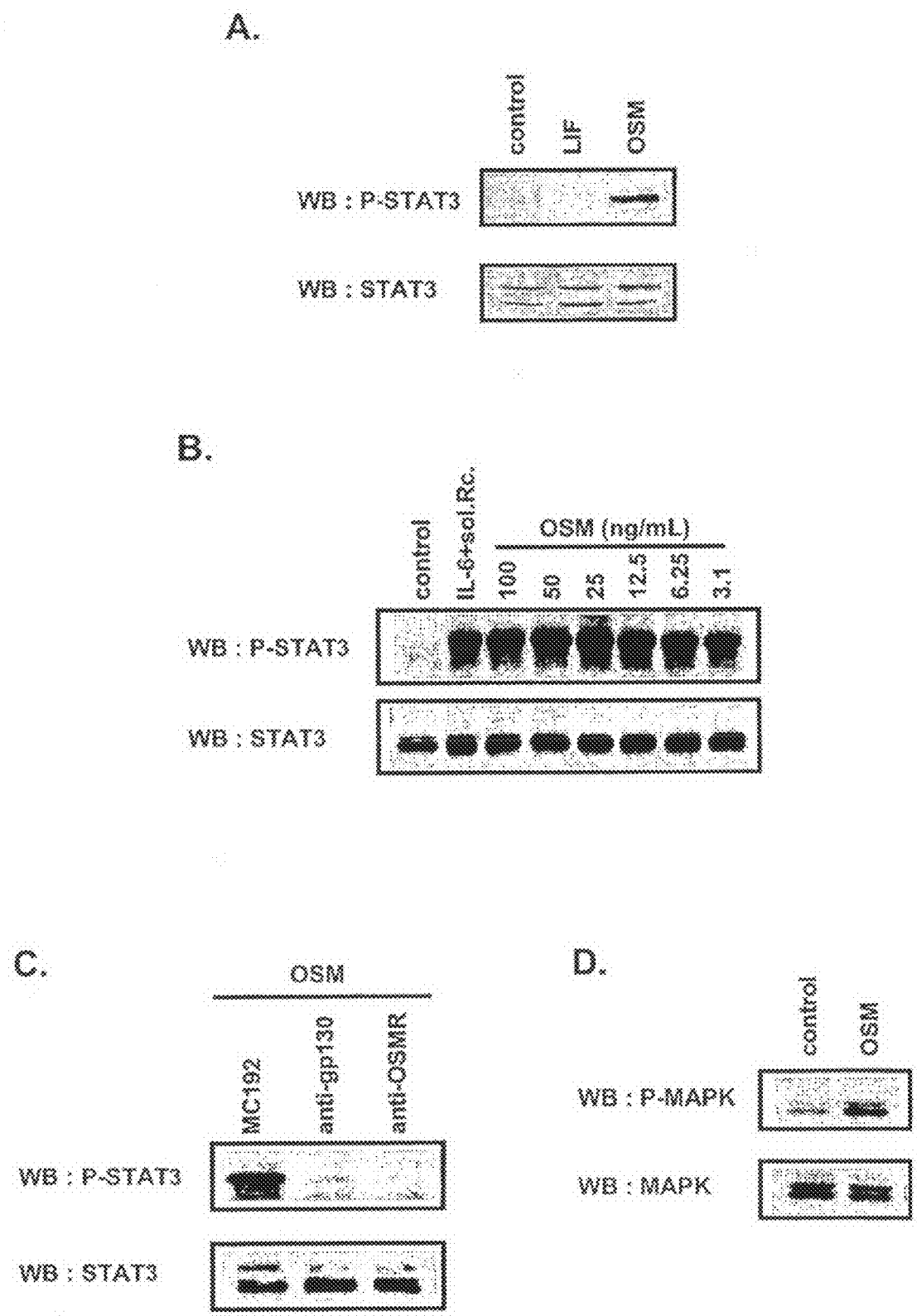

FIG. 2 shows the induction of STAT3 and MAP kinase phosphorylation by OSM in NHEK.

(A) NHEK were stimulated or not with LIF or OSM (50 ng/ml). (B) NHEK were stimulated or not for 15 min with 50 ng/ml of IL-5 (negative control) or with 100, 50, 25, 12.5, 6.25 or 3.1 ng/ml of OSM, and phospho-STAT3 (P-STAT3) and STAT3 protein levels were assessed by Western blot. Before stimulation with the cytokines, cells were incubated for 2 h in the presence of neutralizing antibodies, an anti-gp130 (AN-HH1), or an anti-OSMR (XR-M70) monoclonal antibody, or with an isotype control mAb MC192 (final antibody concentration, 15 μg/ml (C). Phospho-MAPK (P-MAPK) and MAPK protein levels in response to OSM was assessed by Western blot (D).

Figure 3:
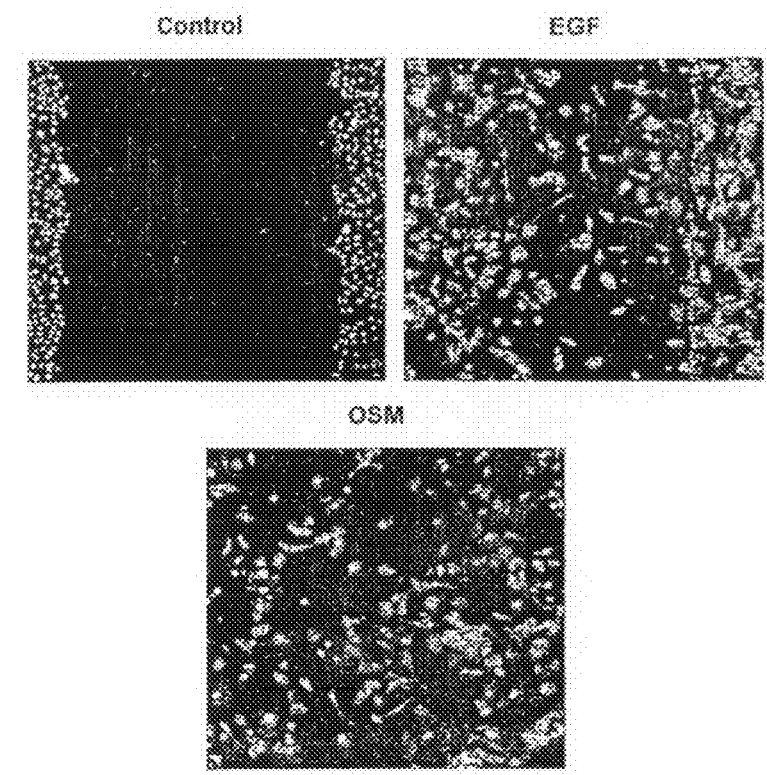
Figure 3:
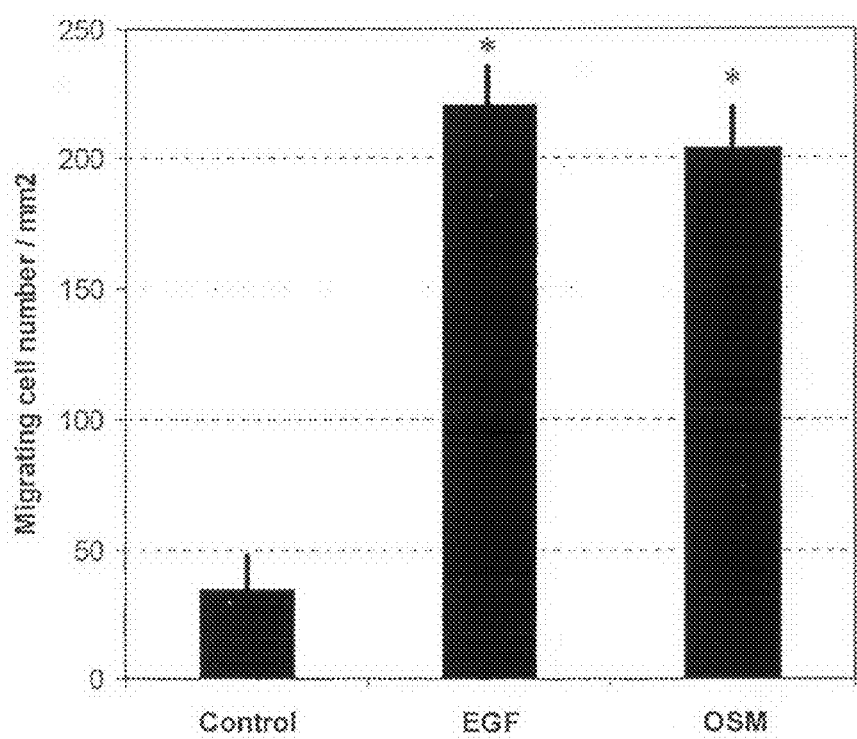

FIG. 3 shows the effect of OSM on keratinocyte migration.

In vitro wounds were introduced in mitomycin-treated confluent NHEK culture and the keratinocytes were cultured for 48 h with or without 10 ng/ml of EGF or OSM. Cell migration to the cell free area was assessed as described in Materials and Methods. Each bar represents the mean±SEM of migrating keratinocytes counted in 4 non-overlapping fields. One experiment representative of 2.

p<0.001 compared with respective control without cytokine, based on Student's t test.

Figure 4:
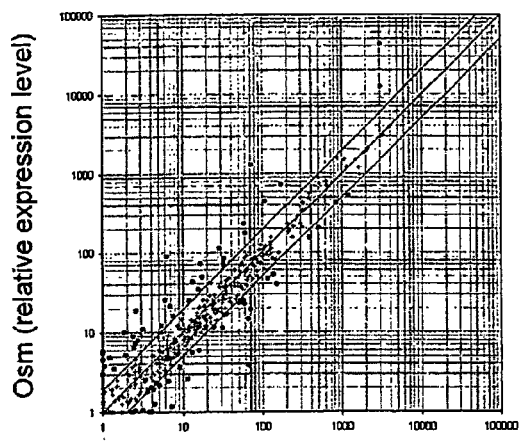
Figure 4:
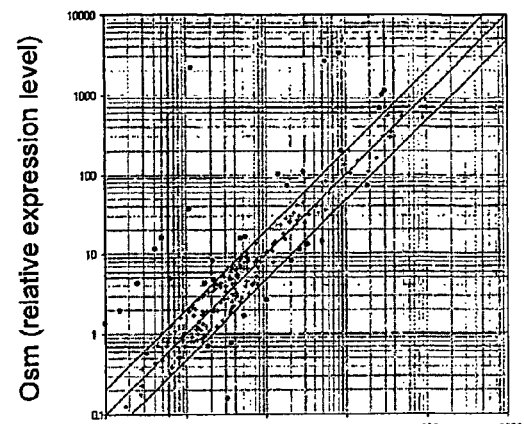

FIG. 4 shows expression profiles obtained from OSM stimulated NHEK and OSM treated RHE.

NHEK (A) or RHE (B) were cultured with or without 10 ng/ml of OSM for 24 h. Total RNA was isolated, treated with Dnase I, and used to make $^{33}$P-labelled cDNA probes, which were hybridized to cDNA arrays. The computer images were obtained after 5 days exposure to a Molecular Dynamics Storm storage screen and further scanning. After local background substraction, an average signal intensity from duplicate spots was normalized for differences in probe labelling using the values obtained for housekeeping genes. (C) The OSM-induced modulation was expressed as the percentage ratio of the signal intensities for cells treated with each cytokine over the signal intensity for unstimulated cells.

Figure 5:
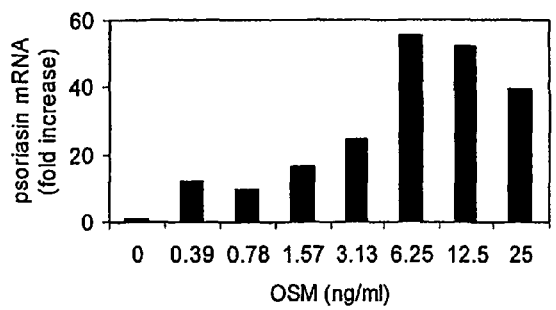
Figure 5:
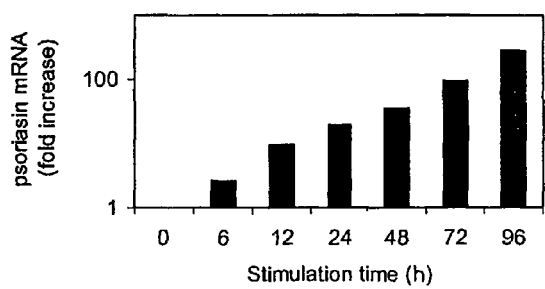
Figure 5:
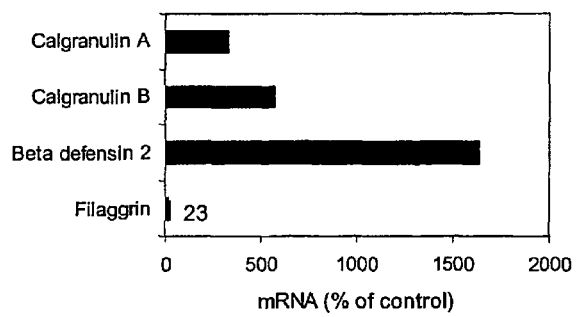
Figure 5:
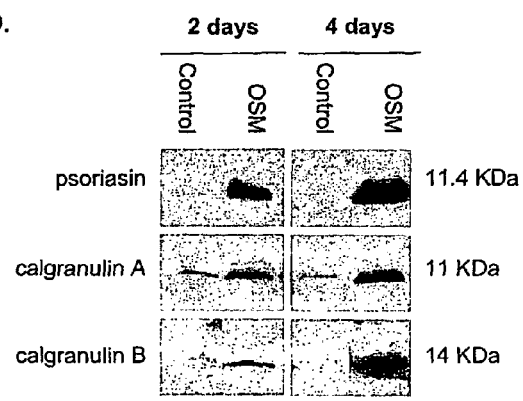

FIG. 5 shows the effect of OSM on S100A7-9 synthesis by NHEK.

NHEK were cultured with or without 0.4, 0.8, 1.6, 3.1, 6.3, 12.5 or 25 ng/ml of OSM for 48 h (A) or with or without 10 ng/ml of OSM for 6, 12, 24, 48, 72, 96 h (B). Total RNA was extracted, reverse transcribed, and S100A7 and HMBS mRNA relative expression was quantified by real time PCR. HMBS was used as a housekeeping gene to normalize gene expression as detailed in Materials and Methods. Results, expressed as the relative expression of stimulated cells over control cells, are representative of 2 independent experiments. (C) NHEK were cultured with or without 10 ng/ml of OSM for 48 h. Relative S100A8-calgranulin A, S100A9-calgranulin B, β-defensin 2 and filaggrin mRNA expression was quantified by quantitative RT-PCR. Results are expressed as the relative expression of stimulated cells over control cells. (D) NHEK were cultured with or without 10 ng/ml of OSM for 48 and 96 h. Twenty μg of cell lysate were separated by SDS-PAGE (16%) and transferred to nitrocellulose membrane. Ponceau red staining was used to control loading homogeneity. S100A7, S100A8 and S100A9 protein levels was determined by Western blot. The results are representative of 3 independent experiments.

Figure 6:
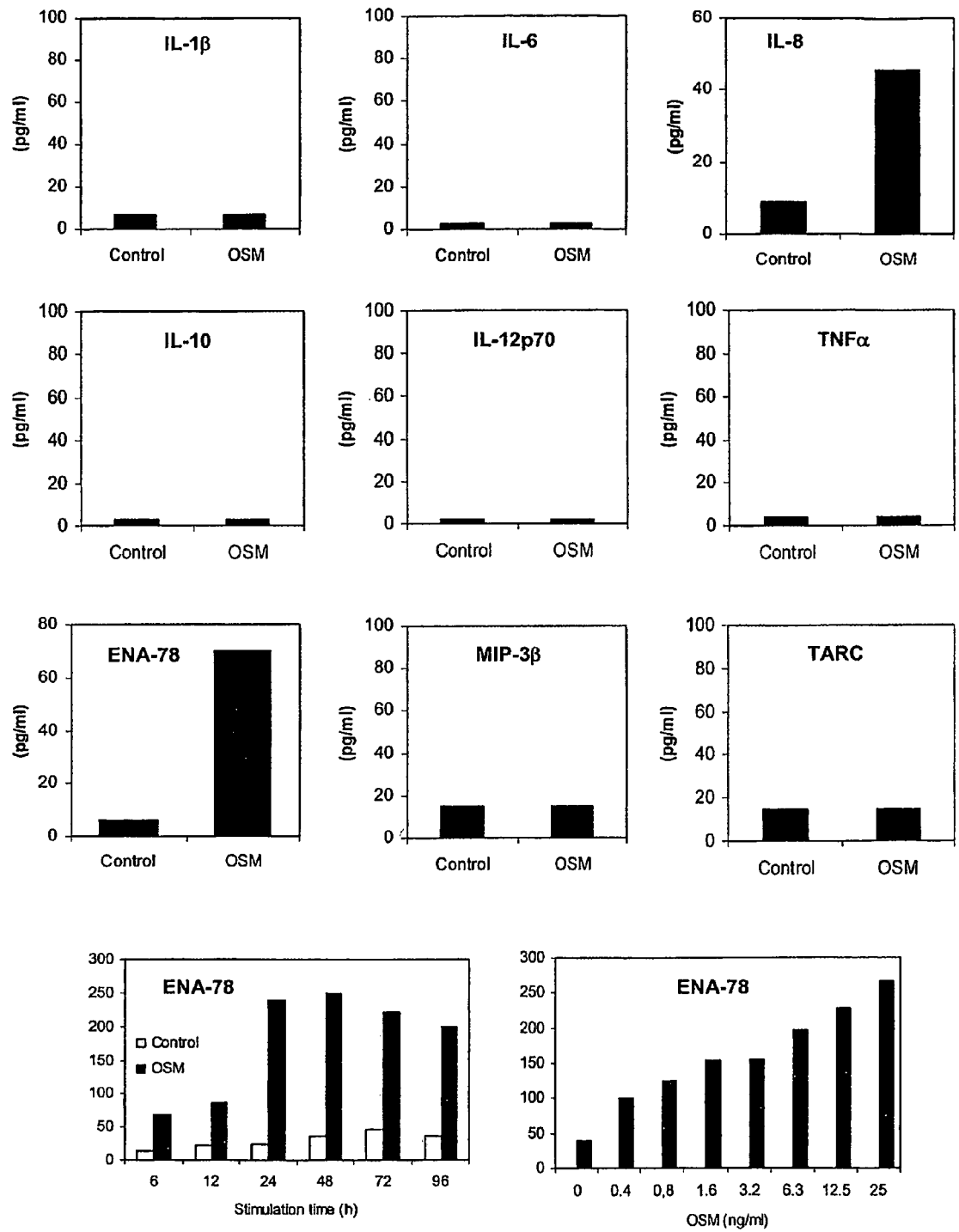

FIG. 6 shows cytokines and chemokines production by NHEK. IL-1beta, IL-6, IL-8, IL-10, IL-12p70, TNF alpha, ENA-78, MIP 3 beta were measured by specific ELISA in 48 h NHEK culture supernatants. Cells were cultured in the presence or not of OSM. Dose-response (0.4 to 25 ng/ml) and kinetic (6 to 96 h) studies of ENA78 production were also performed.

Figure 7:
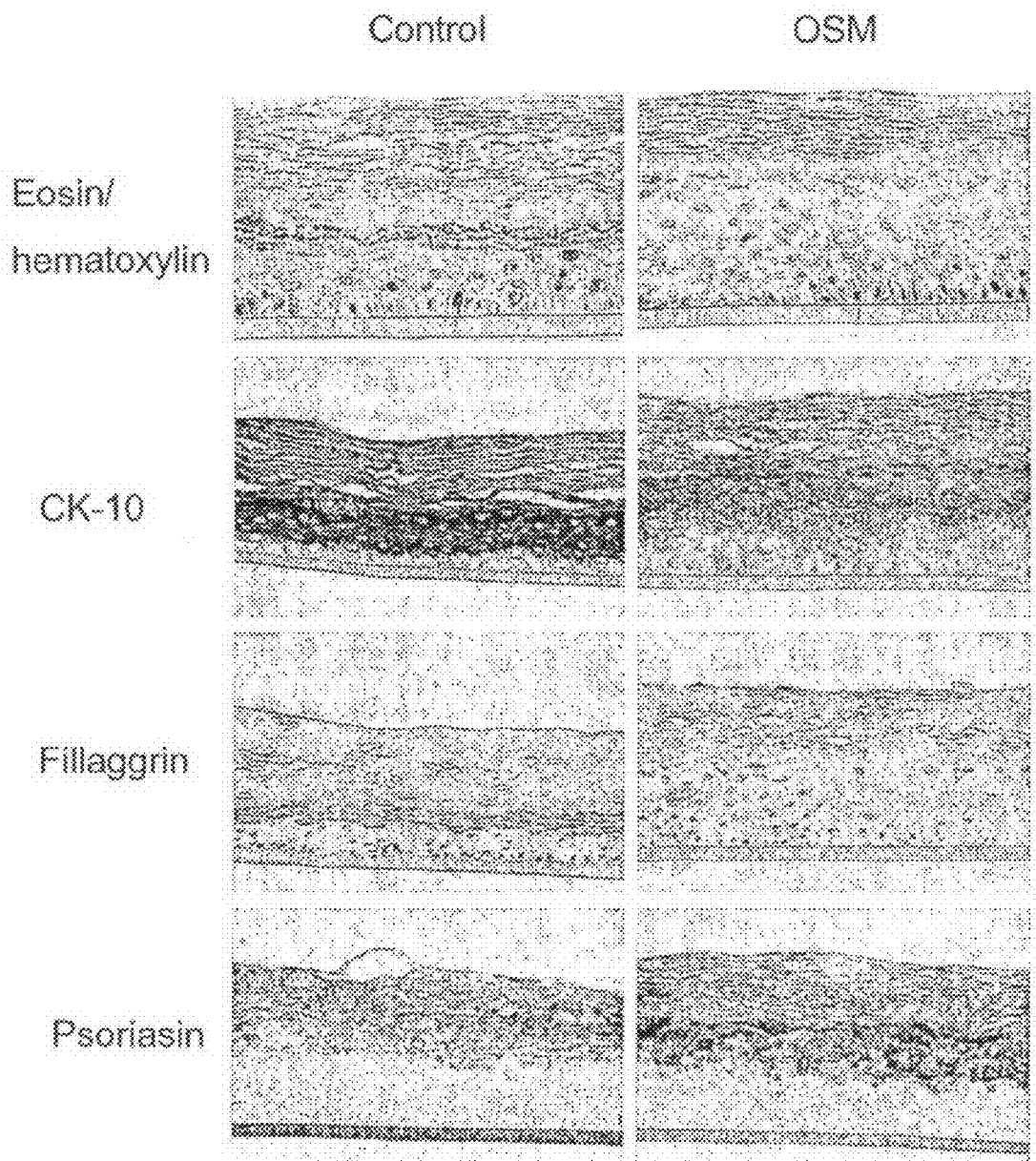

FIG. 7 shows histological and immunohistochemical analysis of RHE stimulated or not with 10 ng/ml of OSM for 4 days. RHE were fixed, embedded in paraffin. Four micron vertical sections were stained with hematoxylin/eosin or reacted with anti-K10 keratin mAb, anti-filaggrin mAb or anti-S100A7 mAb and then photographed under a microscope (magnification×200).

Figure 8:
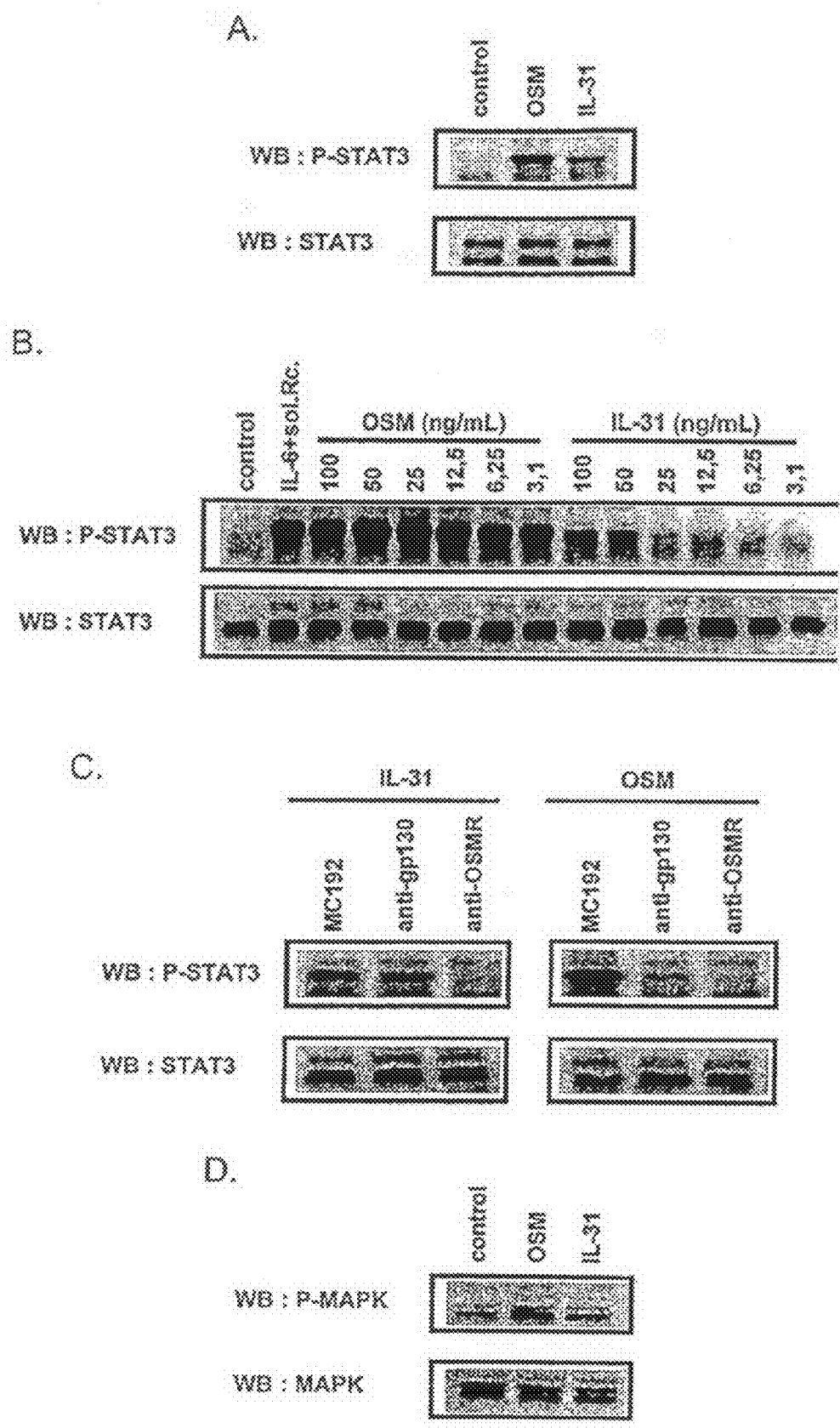

FIG. 8 shows induction of STAT3 and MAP kinase phosphorylation by IL-31 and OSM in NHEK.

NHEK were stimulated or not for 15 min with 10 ng/ml of OSM, or with 100 ng/ml of IL-31 (A), or with different concentrations of these cytokines (B), and phospho-STAT3 (P-STAT3) and STAT3 protein levels were assessed by Western blot. Before stimulation with the cytokines, cells were incubated for 2 h in the presence of neutralizing antibodies, an anti-gp130 (AN-HH1), or an anti-OSMR (XR-M70) monoclonal antibody, or with an isotype control mAb MC192 (final antibody concentration, 15 µg/ml) (C). Phospho-MAPK (P-MAPK) and MAPK protein levels in response to IL-31 and OSM was assessed by Western blot (D).

Figure 9:
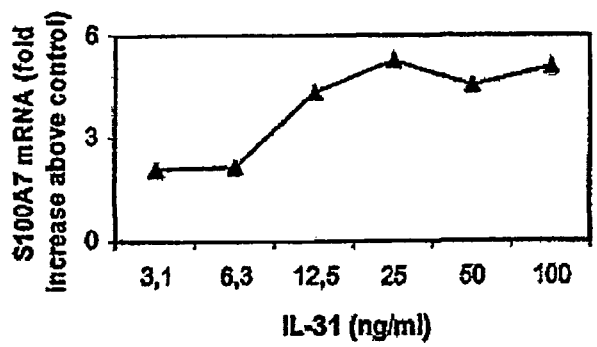
Figure 9:
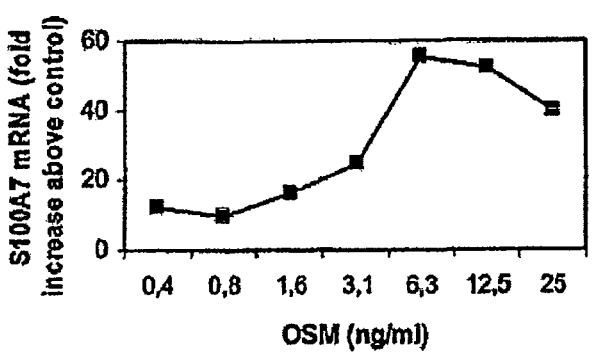
Figure 9:
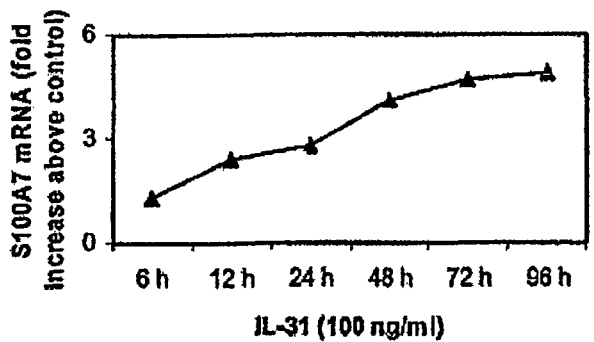
Figure 9:
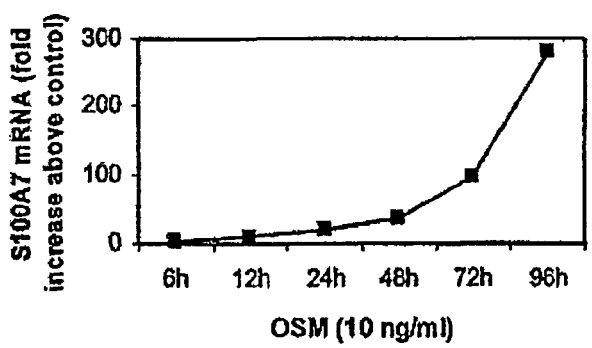

FIG. 9 shows the effect of IL-31 and OSM on S100A7 mRNA expression.

NHEK were cultured with or without 3.1, 6.3, 12.5, 25, 50 or 100 ng/ml of IL-31 (A) or with or without 0.4, 0.8, 1.6, 3.1, 6.3, 12.5 or 25 ng/ml of OSM (B) for 48 h. Kinetic study of S100A7 mRNA expression in the absence or presence of 100 ng/ml of IL-31 (C) or 10 ng/ml of OSM (D). Total RNA was extracted, reverse transcribed, and S100A7 and HMBS mRNA relative expression was quantified by real time PCR. HMBS was used as a housekeeping gene to normalize gene expression as detailed in Materials and Methods. Results, expressed as the relative expression of stimulated cells over control cells, are representative of 2 independent experiments.

Figure 10:
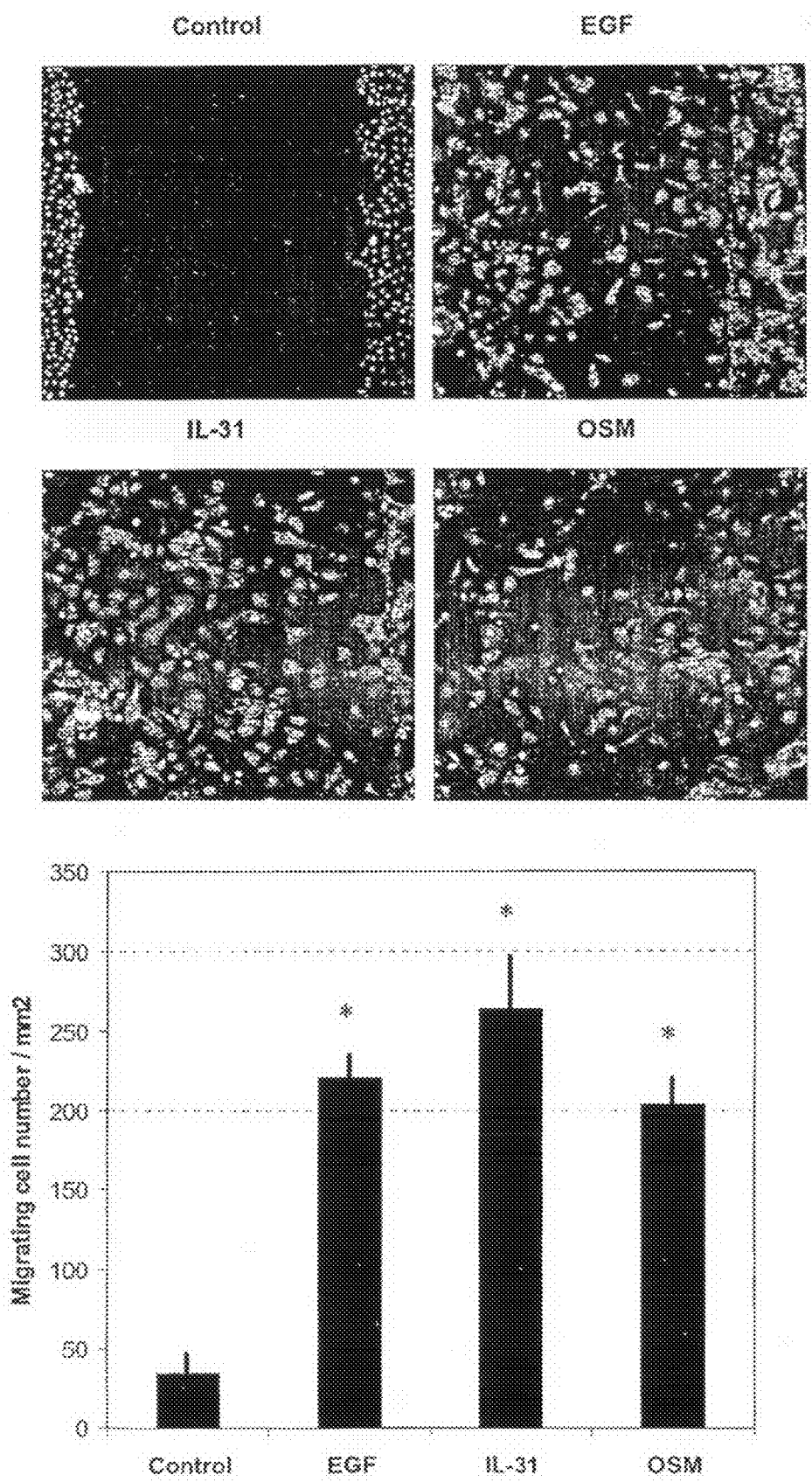

FIG. 10 shows the effect of IL-31 and OSM on keratinocyte migration.

In vitro wounds were introduced in mitomycin-treated confluent NHEK culture and the keratinocytes were cultured for 48 h with or without 100 ng/ml of IL-31, or 10 ng/ml of EGF or OSM. Cell migration to the cell free area was assessed as described in Materials and Methods. Each bar represents the mean±SEM of migrating keratinocytes counted in 4 non-overlapping fields. One experiment representative of 2. *p<0.001 compared with respective control without cytokine, based on Student's t test.

Figure 11:
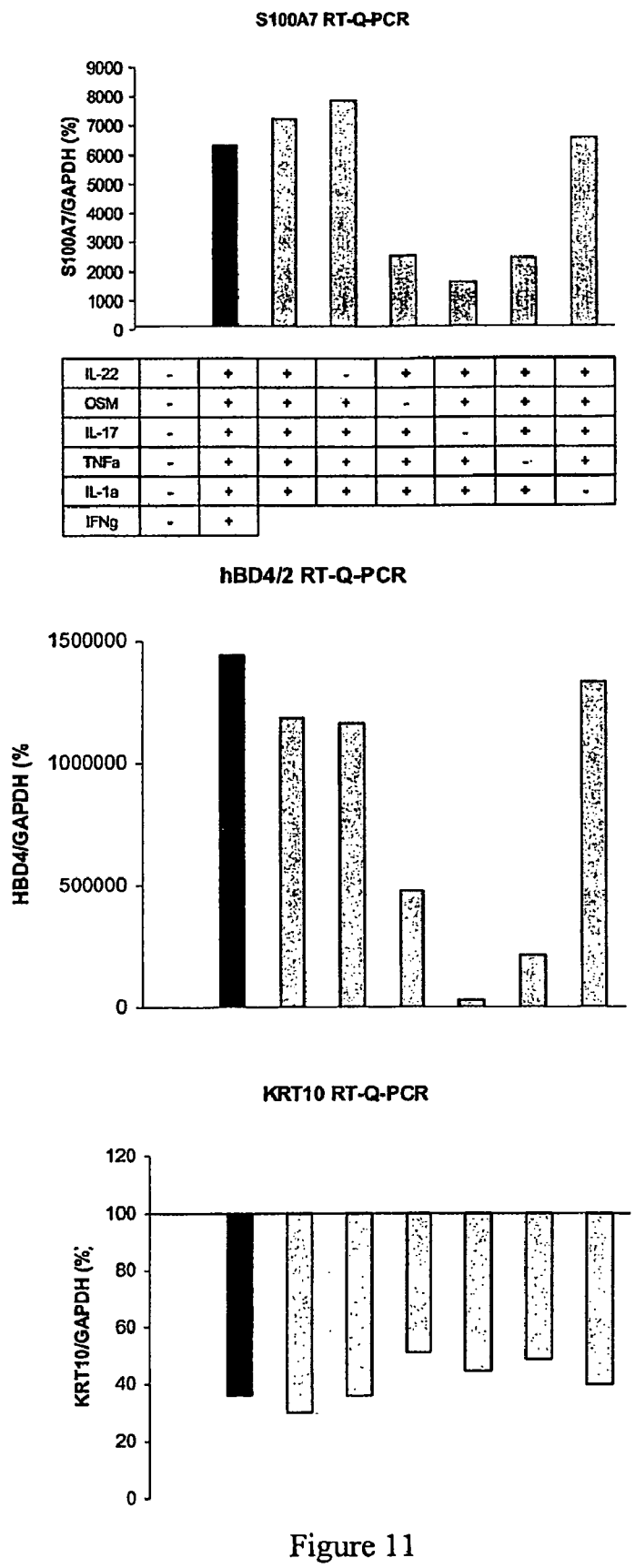

FIG. 11 shows the effect of several cocktails of cytokines on S100A7, hBD4/2, and KRT10mRNA expression.

Confluent normal human keratinocytes (NHEK) were treated for 24 hrs with the indicated mixed cytokine (each cytokine at 1 ng/ml final concentration). Total RNA was extracted, reverse-transcribed and the expression of the selected genes was analyzed by real-time PCR.

Example 1

Material and Methods

Cell Cultures, Cytokines and Reagents

NHEK were obtained from surgical samples of healthy breast skin. The use of these samples for research studies was approved by the Ethical Committee of the Poitiers Hospital. Skin samples were incubated overnight at 4° C. in a dispase solution (25 U/ml; Invitrogen Life Technologies, Cergy Pontoise, France). Epidermal sheets were removed from dermis and NHEK were dissociated by trypsin digestion (trypsin-EDTA, Invitrogen) for 15 min at 37° C. Cells were cultured in Serum-Free Keratinocyte Medium (Keratinocyte SFM) supplemented with bovine pituitary extract (25 µg/ml) and recombinant epidermal growth factor (0.25 ng/ml; all purchased from Invitrogen). NHEK were starved for 48 h in Keratinocyte SFM without addition of growth factors before stimulation.

Human recombinant OSM, IL-5, IL-6, soluble IL-6R were purchased from R&D Systems (Oxon, UK). The IgG1 isotype control (MC192), anti-gp130 (AN-HH1), anti-OSMR antibody (AN-A2) and anti-LIFR (AN-E1) were produced in the laboratory. Antibodies raised against phospho-STAT3, phospho-MAPK, MAPK were bought from Upstate Biotechnology (Lake Placid, N.Y.). Anti-STAT3, anti-S100A8 and anti-S100A9 antibodies were from Santa Cruz Biotechnology (Santa Cruz, Calif., USA). Anti-S1000A7 antibody was purchased from Imgenex (San Diego, Calif., USA). Goat anti-mouse and anti-rabbit peroxidase labelled immunoglobulins were from Cliniciences (Montrouge, France), and rabbit anti-goat peroxidase-conjugated antibody was from Sigma (Amersham Biosciences).

RT-PCR and RT-Real Time PCR Analysis

Total cellular RNA was isolated using Trizol reagent (Invitrogen) and treated with DNase I (0.05 U/µl; Clontech, Palo Alto, Calif., USA). cDNAs were synthesised from 2 µg of total RNA by random hexamer primers using MMLV reverse transcriptase (Promega, Madison, Wis.). Reverse transcription products were subsequently amplified by 25 cycles of PCR using primers for OSMR (forward 5'-CCTGCCTACCT-GAAAACCAG-3' (SEQ ID No: 1) and reverse 5'-ACATTG-GTGCCTTCTTCCAC-3' (SEQ ID No: 2)), gp130 (forward 5'-GGGCAATATGACTCTTTGAAGG-3' (SEQ ID No: 3) and reverse 5'-TTCCTGTTGATGTTCAGAATGG-3' (SEQ ID No: 4)), LIFR (forward 5'-CAGTACAAGAGCAGCG-GAAT-3' (SEQ ID No: 5) and reverse 5'-CCAGTCCATAAG-GCATGGTT-3' (SEQ ID No: 6)) and GAPDH (forward 5'-ACCACAGTCCATGCCATCAC-3' (SEQ ID No: 7) and reverse TCCACCACCCTGTTGCTGTA (SEQ ID No: 8)). Amplified products were analysed by 2% agarose gel electrophoresis.

Quantitative real time PCR was carried out using the LightCycler-FastStart DNA Master$^{PLUS}$ SYBR Green I kit (Roche, Mannheim, Germany). The reaction components were 1X FastStart DNA Master$^{PLUS}$ SYBR Green I and 0.5 µM of forward and reverse primers for S100A7 (forward 5'-GCAT-GATCGACATGTTTCACAAATACAC-3' (SEQ ID No: 9) and reverse 5'-TGGTAGTCTGTGGCTATGTCTCCC-3' (SEQ ID No: 10)), S100A8 (Pattyn, Speleman et al. 2003), S100A9 (forward 5'-GCTCCTCGGCTTTGACAGAGTG-CAAG-3' (SEQ ID No: 11) and reverse 5'-GCATTTGTGTC-CAGGTCCTCCATGATGTGT-3' (SEQ ID No: 12)), hBD2/4 (forward 5'-GCCATCAGCCATGAGGGTCTTG-3' (SEQ ID No: 13) and reverse 5'-AATCCGCATCAGCCA-CAGCAG-3' (SEQ ID No: 14)), KRT10 (forward 5'-GC-CCGACGGTAGAGTTCTTT-3' (SEQ ID No: 15) and reverse 5'-CAGAAACCACAAAACACCTTG-3' (SEQ ID No: 16)), and hydroxymethyl-bilane synthase (HMBS) as a housekeeping gene (Vandesompele, De Preter et al. 2002). After cDNA fluorescent quantification using propidium iodide, 250 ng, 25 ng and 2.5 ng of cDNA were added as PCR template in the LightCycler glass capillaries. The cycling conditions comprised a 10 min polymerase activation at 95° C. and 50 cycles at 95° C. for 10 s, 64° C. for 5 s and 72° C. for 18 s with a single fluorescence measurement. Melting curve analysis, obtained by increasing temperature from 60° C. to 95° C. with a heating rate of 0.1° C. per second and a continuous fluorescence measurement, revealed a single narrow peak of suspected fusion temperature. A mathematical model was used to determine the relative quantification of target genes compared to HMBS reference gene (Pfaffl 2001).

Gene Expression Profiling Using cDNA Macroarrays

Total RNA was isolated as described for PCR studies. DNase treatment, polyA+ RNA enrichment, $^{33}$P-labelled cDNA probe synthesis, purification and hybridization to custom Atlas array membranes (Bernard, Pedretti et al. 2002) were performed according to Clontech's recommendations (Clontech, Palo Alto, USA). Membranes were exposed for 5 days to a Molecular Dynamics Storm storage screen and scanned using a phosphorimager scanner (Molecular Dynamics Storm analyser, Amersham Biosciences, Uppsala, Sweden). After local background substraction, average signal intensity from duplicate spots was normalized for differences in probe labelling using the values obtained for housekeeping genes (Bernard et al., 2002). For each gene, the OSM-induced modulation was expressed as the relative expression value for stimulated versus control sample. Arbitrarily, only modulation above 2 was considered significant for confirmation using RT-real time PCR assay.

Western Blotting Analysis

For STAT3 and MAPK phosphorylation, NHEK were stimulated for 15 min in the presence of the indicated cytokine. Cells were lysed in SDS sample buffer (62.5 mM Tris-HCl pH 6.8, 2% SDS, 10% glycerol, 50 mM DTT, 0.1% bromophenol blue), sonicated and then submitted to SDS-PAGE and transferred onto an Immobilon membrane. The membranes were subsequently incubated overnight with the primary antibody, before being incubated with the appropriate peroxidase-labelled secondary antibody for 60 min. The reaction was visualized by chemiluminescence according to the manufacturer's instructions. Membranes were stripped in 0.1 M glycine pH 2.8 for 2 h and neutralized in 1 M Tris-HCl pH 7.6 before reblotting. For neutralizing experiments, NHEK were incubated with the appropriate antibodies for 2 h before stimulation.

To determine the expression of gp130, LIFR and OSMR, the cells were lysed in 10 mM Tris HCl pH 7.6, 5 mM EDTA, 50 mM NaCl, 30 mM sodium pyrophosphate, 50 mM sodium fluoride, 1 mM sodium orthovanadate proteinase inhibitor and 1% Brij 96. After lysis and centrifugation to remove cellular debris, the supernatants were then treated as described above.

For S100 proteins expression, NHEK were stimulated for 2 days in the presence of OSM (10 ng/ml). Cell lysis was performed with 50 mM Tris HCl pH 7.4, 150 mM NaCl, 1 mM EDTA, 1% Triton, 1% sodium deoxycholate, 0.1% SDS, 1 mM PMSF, 1 mM sodium orthovanadate, 1% protease inhibitors. S100A7, S100A8 and S100A9 were detected by immunochemistry as described above. Ponceau red staining was used to control loading homogeneity.

In Vitro Keratinocyte Migration Assay

Keratinocytes were cultured in wells pre-coated with type I collagen (200 µg/ml, Institut Jacques Boy, Reims, France) until they reached 80% confluency. Cells were starved for 48 h in Keratinocyte SFM and then treated with 10 µg/ml of mitomycin C (Sigma) for 2 h to prevent cell proliferation. A cell-free area was created by scraping the keratinocyte monolayer with a plastic pipette tip. Keratinocytes migration to the cell-free area was evaluated after 48 h of culture in the absence or presence of EGF or OSM. Using an inverted phase contrast microscope. The number of migrating keratinocytes was counted in 4 non-overlapping fields. Values represent the mean±SEM of cells per mm$^2$ beyond the frontiers of the in vitro injury. Student's t test was used for statistical analysis.

Reconstituted Human Epidermis Model

For histological and immunohistochemical studies, RHE, grown for 12 days at the air-medium interface, were purchased from SkinEthic Laboratories (Nice, France). They consist of a multi-layered epidermis which exhibit morphological and growth characteristics similar to human skin (Rosdy, Bertino et al. 1997). As recommended, RHE were grown for 1 day in SkinEthic growth medium prior to stimulation in the absence or presence of OSM for 4 days. They were then fixed in a balanced 10% formalin solution and embedded in paraffin. Four micron vertical sections were stained with heamatoxylin/eosin or with specific Ab and peroxidase-conjugated Antibodies, and counterstained with haematoxylin according to standard protocols (Rosdy, Bertino et al. 1997). Anti-K10 keratin and anti-filaggrin monoclonal Antibodies were from Lab Vision Corporation (Fremont, Calif., USA).

For gene expression profiling using cDNA macroarrays, 17 days old RHE were grown for 1 day in SkinEthic maintenance medium prior to stimulation in the absence or presence of OSM for 24 h. Total RNA was isolated and cDNA arrays were performed as described above.

Example 2

Human Keratinocytes Expressed the Type OSM Receptor on Their Surface

To show the potential functions of OSM in normal human keratinocytes the inventors first undertook an analysis of its receptor chain expression. To determine the nature of expressed type I or type II receptors, RT-PCR for gp130, LIFRβ and OSMRβ were carried out starting from primary cultures of keratinocytes. CO-G-UVM and glioblastoma cells were used as controls for LIFR. Obtained results show that NHEK predominantly expressed transcripts for OSMR and the gp130, whereas only low levels of the LIFR chain could be evidenced (FIG. 1A). The RNA analysis was further reinforced by measuring the expression levels of corresponding proteins by flow cytometry. Fluorescence analyses revealed a clear expression of gp130 and OSMRβ on the NHEK cell surface (FIG. 1B). In contrast no detection of membrane LIFRβ expression could be evidenced, whereas the anti-LIFRβ antibody gave the expected result when incubated with a cell line used as a positive control. This was further supported by western blot analyses showing the detection of gp130 and OSMRβ chains, and an absence of LIFRβ expression in NHEK (FIG. 1C). Similar experiments carried out on samples coming from four different donors led to the same results, ruling out the possibility for variations in type I or type II OSM receptor expression from donor to donor. These first results indicate that human keratinocytes preferentially expressed the specific type II OSM receptor.

Example 3

STAT-3 and MAP Kinase Pathways are Recruited by OSM in Human Keratinocytes

The inventors show OSM-induced signal transduction in NHEK. Since STAT3 is usually recruited by the OSM type II receptor pathway, they analyzed the tyrosine phosphorylation of the signaling molecule in response to increasing concentrations of the cytokine. A strong induction of tyrosine phosphorylation was observed for STAT3, with plateau level values still present down to 3 ng/ml OSM (FIG. 2B). The involvment of gp130 and OSMRβ subunits was further demonstrated by blocking of the STAT3 phosphorylation when adding receptor neutralizing mAbs to the NHEK culture before OSM contact (FIG. 2C). Importantly, the complete neutralization of STAT3 phosphorylation observed in the presence of the anti-OSMRβ mAb further demonstrated the absence of recruitment by OSM of the share LIF/OSM type I receptor in NHEK. In agreement with this observation, after a LIF contact no evidence for a STAT3 activation could be observed in NHEK.

In addition, type II OSM receptor complex is also known to be a more potent activator for the recruitment of the Map kinase pathway compared to the shared LIF/OSM receptor. A cooperative effect between ERK1/ERK2 and the Shc adaptor, and mediated through OSMRβ, but not through the LIFRb, explains this strong activation the MAP kinase pathway in response to OSM (Boulton, Stahl et al. 1994). The ERK1/2 signaling in response to the cytokine in NHEK was therefore analyzed by determining their tyrosine phosphorylation level. As expected, NHEK stimulation with OSM quickly increased the MAP kinase phosphorylation (FIG. 2D). Taken together, these results demonstrated that gp130/OSMRβ receptor complex expressed in human keratinocytes is fully functional, and that the entire observed signals are mediated through the type II receptor.

Example 4

OSM is a Potent Inducer of Keratinocyte Migration

To underline the functional responses of NEHK to OSM, The inventors analyzed the potential effect of OSM on an in vitro model mimicking the wound healing and based on the keratinocyte migration (Kira, Sano et al. 2002). Forty eight hours after initiation of the culture, cells present in the middle of the well were removed by scratching, and the remaining keratinocytes were stimulated with either EGF, known to trigger the keratinocyte migration, or with OSM. After an additional 36 h of culture, the cytokine potential for inducing cell migration was visually determined or by cell counting (FIG. 3). Obtained results show that OSM led to an important migration of NHEK, similar to that observed in the presence of EGF.

Example 5

Identification of OSM-Induced Gene Expression in Human Keratinocytes

To have a better view of the NHEK functional response the inventors analyzed the modification of keratinocyte gene expression profile induced by OSM using cDNA arrays. Used arrays were specially designed for the study of keratinocytes, and consisting of 586 different cDNAs spotted in duplicate. They consisted in genes involved in keratinocyte cell structure, metabolism, extracellular matrix, adhesion, differentiation, signaling, signal transduction, apoptosis and stress (Bernard et al., 2002). RNA extracted from control or OSM-stimulated NHEK were used to generate labeled cDNA probes by reverse transcription. Probing the Atlas cDNA array membranes with these cDNA probes revealed that OSM increased the expression of 36 genes and decreased the expression of 38 genes. OSM down regulates a large set of genes associated with keratinocyte differentiation, such as cytokeratin (CK)1, CK10, fillagrin and loricrin genes. Among the up-regulated genes, the inventors found a marked increase for the calcium binding proteins, psoriasin (S100A7), calgranulins (S100A8, S100A9) and the S100 neutrophil protein (FIG. 4). Interestingly, the expression of these proteins is known to be up-regulated in inflammatory tissues (Madsen, Rasmussen et al. 1991; Nagase and Woessner 1999; Roth, Vogl et al. 2003). OSM also induced the G-protein-coupled receptor HM74, the super oxyde dismutase 2 and the beta-defensin genes, involved in tissue protection. Genes involved in tissue remodelling such as matrix metalloproteinase 1 and tenascin were also induced by OSM. In addition, OSM increased the expression of the chemokines CXCL1 (MIP-2α), CXCL5 (epithelial-derived neutrophil-activating peptide (ENA 78) and CXCL8 (IL-8), and the platelet-derived growth factor A (PDGF-A) genes.

Obtained results indicate that, in human keratinocytes, OSM was able to recruit a number of genes involved in inflammatory processes and in innate immune response.

Example 6

OSM Induced Keratinocytes to Produce Psoriasin, Calgranulin, βdefensin, and Chemokines To further reinforce the results obtained using designed-arrays, quantitative analyses at mRNA and protein levels were carried out for a selected number of identified genes. Quantitative analysis of psoriasin/S100A7 mRNA expression in response to OSM was performed by RT-real-time PCR along kinetic and dose-response studies. The inventors show that psoriasin/S100A7 mRNA was up-regulated in a dose-dependent manner in response to OSM ranging from 1.6 to 6.3 ng/ml after a 48-h treatment, and the plateau was reached for 6.3 ng/ml OSM with a fifty fold increase of the signal above control (FIG. 5A). Kinetic study revealed an increase in psoriasin/S100A7 mRNA expression starting at 12 h following stimulation with 10 ng/ml of OSM (FIG. 5B). It still increased up to 96 h, with a strong induction of about 290 folds above the control value. This was confirmed at the protein level by western blot analyses of the psoriasin/S100A7, as well as of two related calcium binding proteins, the S100A8 and S100A 9 calgranulins (FIG. 5D). Results show that NHEK exposure to 10 ng/ml of OSM resulted in an increased expression of studied proteins that was strongest at day 4 than at day 2 (FIG. 5D). FIG. 5C depicts the results obtained by analyzing the RNA quantitative expression of filagrin and βdefensin-2, two important markers of skin activation.

The production of the chemokines CXCL5 and CXCL8 in 48 h NHEK is also clearly enhanced under OSM stimulation (FIG. 6B).

Example 7

OSM Triggers Hyperplasia of Reconstituted Human Epidermis and Modulates the Expression of Differentiation Related Antigens To further approach the dynamic of epidermal differentiation, the inventors tested the biological effect of OSM on in vitro RHE in order to assess the basal cell layer proliferation and the graduated epidermal differentiation processes. Histological analysis of control RHE showed a keratinised multi-stratified epithelium resembling epidermis in vivo, containing intact basal, spinous, granulous and cornified cell-layers, and numerous keratohyalin granules in the upper granular layer (FIG. 7). OSM triggered the hyperplasia of the keratinocytes layers, leading to an increase in the overall thickness of the RHE. In addition, they observed a loss of keratohyalin granules in the granular layer and the presence of picnotic nuclei. cDNA array profile analysis of RHE confirmed that OSM strongly up-regulated S100A7, S100A8, S100A9 and S100 neutrophil protein genes, as previously described on NHEK (FIG. 4). By immunohistochemistry, we confirmed the S100A7 protein up-regulation in OSM-treated RHE (FIG. 7). In agreement with the data on NHEK, OSM treatment on RHE also up-regulated CXCL5, CXCL8 chemokine genes, and the PDGF-A and the cadherin 3 gene transcription. Specific to RHE but not detected in NHEK, OSM up-regulated the CK6A, 6B, 6D, 7, 13, 14, 16, the skin-derived antileukoproteinase and the TGFβ-inducible early protein.

On the other hand, OSM down-regulates genes associated with keratinocyte differentiation, such as involucrin, filaggrin, and calmodulin-like skin protein (Mehul, Bernard et al. 2000; Rogers, Kobayashi et al. 2001; Jonak, Klosner et al. 2002; Wagener, van Beurden et al. 2003). Immunohistochemical analysis performed on RHE sections confirmed the inhibition of keratinocyte differentiation, as indicated by the decrease of filaggrin and keratin 10 expression in OSM treated RHE (FIG. 7).

Example 8

Discussion

The use of a cDNA array approach, specially designed for the analysis of gene expression in human skin, enabled the identification of OSM target genes in human keratinocytes and the demonstration of the involvement of OSM in a variety of processes, including migration and differentiation. In particular, the strong, dose dependent, OSM-mediated induction of the expression of S100A7, S100A8 and S100A9 proteins in NHEK and RHE demonstrates the pro-inflammatory and chemotactic effects of the cytokine. The opposing effects of IL-10 and OSM in cutaneous inflammation are underscored by the IL-10-induced down-regulation of S100A8 and S100A9 release by monocytes (Lugering, Kucharzik et al. 1997). S100A7, S100A8 and S100A9 belong to the pleiotropic S100 family of calcium-binding proteins (Roth, Vogl et al. 2003). Although their main functions are as yet unclear, they appear to play prominent inflammatory functions (Watson, Leygue et al. 1998; Donato 1999; Roth, Vogl et al. 2003) and to be involved in the tight regulation of a large number of intra- and extracellular activities such as the dynamic of motility of cytoskeletal components or chemotaxis (Ryckman, Vandal et al. 2003). Interestingly, whereas all three S100A7, S100A8 and S100A9 proteins have been reported to be expressed at low or undetectable levels in normal skin epidermis and non-differentiated cultured keratinocytes, they are highly expressed in abnormally differentiated psoriatic keratinocytes (Broome, Ryan et al. 2003), during wound repair (Thorey, Roth et al. 2001) and in epithelial skin tumors (Watson, Leygue et al. 1998; Gebhardt, Breitenbach et al. 2002; Alowami, Qing et al. 2003). Because of the chemotactic effects of S100A7 on inflammatory cells, in particular neutrophils and CD4+ T lymphocytes, it has been suggested that S100A7 may be involved in the genesis of psoriatic lesions (Watson, Leygue et al. 1998). Since S100A7 acts upstream of these mechanisms, the inventors demonstrate that OSM is a key molecule for the induction of S100A7 under pathological conditions, and is involved in the pathological state. The modulation of additional genes by OSM is also in favour of the pro-inflammatory and chemotactic roles of OSM. Indeed, the induction of neutrophil attractant chemokine CXCL5/ENA-78 together with the down-regulation of heme oxygenase 1, which antagonizes inflammation by attenuating adhesive interaction and cellular infiltration in skin, could contribute to the neutrophil influx in skin (Koch, Kunkel et al. 1994; Wagener, van Beurden et al. 2003).

OSM-induced MMP-3 expression is also of interest in the context of inflammatory cutaneous diseases and wound repair. Whereas MMP-3 cannot be detected in normal skin, it is expressed by proliferative keratinocytes of the basal layer after injury (Pilcher, Wang et al. 1999). During progression of many diseases, MMP-3 is involved in epidermis remodeling by removal of extracellular matrix during tissue resorption (Nagase and Woessner 1999; Pilcher, Wang et al. 1999), and mice that lack the MMP-3 gene are deficient in wound repair of the epidermis (Bullard, Lund et al. 1999). Using an in vitro wound assay, the inventors demonstrated that keratinocyte migration is strongly increased by OSM stimulation. These data are in agreement with the demonstration that STAT3 deficiency in keratinocytes leads to an impaired migration (Sano, Itami et al. 1999). Under inflammatory conditions, OSM appears to be one essential mediator enhancing keratinocyte migration and wound healing, via MMP-3 or S100A8-S100A9 dependent mechanisms. Additional evidence to establish the involvement of OSM in wound healing is the strong induction of PDGF in RHE, a major proliferative and migratory stimulus for connective tissue during the initiation of skin repair processes (Rollman, Jensen et al. 2003).

The inventors also showed that OSM increases the overall thickness of the keratinocyte layer of RHE. This process seems not to be related to basal cell hyperproliferation since Ki67 expression is not induced in response to OSM, but more likely results from an inhibition of terminal keratinocyte differentiation, as shown by the decreased production of filaggrin, loricrin or involucrin. OSM down-regulates the expression of the calmodulin-like skin protein (CLSP) and calmodulin-related protein NB-1, two members of the calmodulin family, directly related to keratinocyte differentiation (Mehul, Bernard et al. 2001; Rogers, Kobayashi et al. 2001). CLSP binds transglutaminase-3, a key enzyme implicated in the formation and assembly of proteins, such as loricrin or involucrin, to form the cornified cell envelop of the epidermis (Mehul, Bernard et al. 2000). The modulating effects of OSM on the keratin expression profile, i.e., keratin 6 over-expression and keratin 10 inhibition, also supports the notion of an inhibition of epidermal differentiation. Keratin 6 is known to be induced under hyperproliferative and/or inflammatory situations, including wound healing, psoriasis, carcinogenesis, or by agents such as retinoic acid that provoke epidermal hyperplasia (Navarro, Casatorres et al. 1995; Komine, Rao et al. 2000). In contrast, keratin 10, normally expressed in terminally differentiating epidermal keratinocytes, is reduced during wound healing (Paramio, Casanova et al. 1999).

Example 9

Similar Results Obtained With IL-31

Studies presented in examples 3, 4 and 5 have been realized with IL-31 instead of OSM and similar results were obtained: IL-31 recruits STAT3 signaling pathways (FIG. 8) in NHEK and induces expression of psoriasin (S100A) and calgranulin A and B (S100A8-9) (FIG. 9). IL-31 is also able to induce keratinocyte migration (FIG. 10).

Example 10

Gamma Interferon Potentiates the Action of IL-31 on the Signal Transduction

When NHEK were preincubated 24 h in the presence of 50 g/ml of gamma Interferon (INFγ) before IL-31 stimulation (50 ng/ml), P-STAT3 level were increased 3 to 4 folds when compared to NHEK preincubated in medium alone (same studies as those realized for the FIG. 8). This demonstrates that INFγ is a modulator of the action of IL-31 on signal transduction.

Example 11

IL-17 and TNFα Potentiate the Action of OSM on the Expression of Several Inflammation Markers The combined effect of several cytokines on keratinocytes was then tested by measuring the expression of the keratinocyte inflammation markers psoriasin (S100A7), defensin beta-2/beta-4 (hBD2/4) mRNAs, in the presence of various cytokines cocktails. The effect of these cocktails was also tested on keratin 10 (KRT10) mRNA, since KRT10 is a differentiation marker associated with tissue healing.

To that aim, confluent normal human keratinocytes (NHEK) were treated for 24 hrs with the indicated mix of cytokines (each cytokine at 1 ng/ml final concentration). Total RNA was extracted, reverse-transcribed and the expression of the selected genes was analyzed by real-time PCR as described.

The results are shown in Table 1 below and in FIG. 11.

TABLE 1

| | cytokines 1 ng/ml | | | | RT-Q-PCR | | X/GAPDH | | |
|---|---|---|---|---|---|---|---|---|---|
| # mix | IL-22 | OSM | IL-17 | TNFα | IL-1α | IFNγ | S100A7 | hBD2/4 | KRT10 |
| M3 | + | + | + | + | + | + | 6 350 | 1 441 000 | 36 |
| M1 | + | + | + | + | − | + | 5 450 | 1 380 000 | 38 |
| M4 | + | + | + | + | + | − | 7 270 | 1 185 000 | 30 |
| M8 | − | + | + | + | + | − | 7 880 | 1 165 000 | 36 |
| M7 | + | − | + | + | + | − | 2 550 | 475 000 | 51 |
| M6 | + | + | − | + | + | − | 1 610 | 32 585 | 45 |
| M5 | + | + | + | − | + | − | 2 450 | 211 000 | 49 |
| M2 | + | + | + | + | − | − | 6 570 | 1 331 000 | 40 |
| | − | − | − | − | − | − | 100 | 100 | 100 |

The mix of the 6 selected cytokines (M3) exhibited a strong synergic effect on the expression of the keratinocyte inflammation markers psoriasin (S100A7) and defensin beta-2/beta-4 (hBD2/4). As expected, KRT10 expression is lowered in the presence of these cytokines. The depletion of the mixes in either IFNγ, IL-22, or IL-1α, did not significantly decrease the activity of the complete cocktail of cytokines; these cytokines are hence probably not directly involved in the observed synergy. To the contrary:

the omission of OSM from the 5 cytokines reference mix (IFNγ has been omitted because it is inactive) led to a decrease of the activity of the mix by 3-fold for S100A7 and by 2.5-fold for hBD2/4;

the omission of TNFα led to a decrease of the activity of the mix by 3-fold for S100A7 and by 5.6-fold for hBD2/4; and the omission of IL-17 led to a decrease of the activity of the mix by 4.5-fold for S100A7 and by 36-fold for hBD2/4.

These results indicate a strong synergy between OSM, TNFα and IL-17 for a maximal response in keratinocytes.

Hence, it appears that OSM is able to synergize with IL-17 and/or with TNFα. In addition, it is suggested that OSM may act synergistically with IL-17 and/or with TNFα for the acceleration of wound re-epithelialization, even at low cytokine concentrations.

Example 12

OSM Improves the Cutaneous Innate Immune Response

Keratinocytes in the skin of patients with psoriasis produce high levels of anti-microbial peptides (Nomura, Goleva et al. 2003). These peptides, present only at negligible levels in normal skin or in the skin of patients with atopic dermatitis, are essential in the cutaneous innate immune response to invading microorganisms, as shown in animal models of infection (Nizet, Ohtake et al. 2001). The enhanced S100A7-psoriasin gene expression in keratinocytes, following stimulation with OSM, therefore points to a role for OSM in the cutaneous innate immune response, as S100A7-psoriasin has been shown to confer resistance to infection of the skin by *Escherichia coli* (Glaser, Harder et al. 2005). Similarly, β-defensin 2, another protein with anti-microbial activities (Harder, Bartels et al. 1997), is induced by OSM in human keratinocytes. Beta-defensin 2 is expressed at high levels in psoriatic lesions but only at low levels in those observed in atopic dermatitis (Ong, Ohtake et al. 2002). In line with this observation, psoriatic patients are reportedly less susceptible to infections, as compared with patients having atopic dermatitis (Nomura, Goleva et al. 2003).

The results reported in Examples 6 and 11 above hence show that OSM, IL-17 and TNFα are potent keratinocyte activators, and that topic administration of these cytokines, either alone or in combination, can enhance the expression of anti-microbial peptides and improve the cutaneous innate immunity.

REFERENCES

Alowami, S., G. Qing, et al. (2003). "Psoriasin (S100A7) expression is altered during skin tumorigenesis." *BMC Dermatol* 3(1): 1.

Benigni, F., G. Fantuzzi, et al. (1996). "Six different cytokines that share GP130 as a receptor subunit, induce serum amyloid A and potentiate the induction of interleukin-6 and the activation of the hypothalamus-pituitary-adrenal axis by interleukin-1." *Blood* 87(5): 1851-4.

Bernard, F. X., N. Pedretti, et al. (2002). "Comparison of gene expression profiles in human keratinocyte mono-layer cultures, reconstituted epidermis and normal human skin; transcriptional effects of retinoid treatments in reconstituted human epidermis." *Exp Dermatol* 11(1): 59-74.

Bonifati, C., A. Mussi, et al. (1998). "Spontaneous release of leukemia inhibitory factor and oncostatin-M is increased in supernatants of short-term organ cultures from lesional psoriatic skin." *Arch Dermatol Res* 290(1-2): 9-13.

Boulton, T. G., N. Stahl, et al. (1994). "Ciliary neurotrophic factor/leukemia inhibitory factor/interleukin 6/oncostatin M family of cytokines induces tyrosine phosphorylation of a common set of proteins overlapping those induced by other cytokines and growth factors." *J Biol Chem* 269(15): 11648-55.

Broome, A. M., D. Ryan, et al. (2003). "S100 protein subcellular localization during epidermal differentiation and psoriasis." *J Histochem Cytochem* 51(5): 675-85.

Bullard, K. M., L. Lund, et al. (1999). "Impaired wound contraction in stromelysin-1-deficient mice." *Ann Surg* 230 (2): 260-5.

Dillon, S. R., C. Sprecher, et al. (2004). "Interleukin 31, a cytokine produced by activated T cells, induces dermatitis in mice." *Nat Immunol* 5(7): 752-60.

Donato, R. (1999). "Functional roles of S100 proteins, calcium-binding proteins of the EF-hand type." *Biochim Biophys Acta* 1450(3): 191-231.

Gallucci, R. M., P. P. Simeonova, et al. (2000). "Impaired cutaneous wound healing in interleukin-6-deficient and immunosuppressed mice." *Faseb J* 14(15): 2525-31.

Gallucci, R. M., D. K. Sloan, et al. (2004). "Interleukin 6 indirectly induces keratinocyte migration." *J Invest Dermatol* 122(3): 764-72.

Gebhardt, C., U. Breitenbach, et al. (2002). "Calgranulins S100A8 and S100A9 are negatively regulated by glucocorticoids in a c-Fos-dependent manner and overexpressed throughout skin carcinogenesis." *Oncogene* 21(27): 4266-76.

Glaser, R., J. Harder, et al. (2005). "Antimicrobial psoriasin (S100A7) protects human skin from *Escherichia coli* infection." *Nat Immunol* 6(1): 57-64.

Harder, J., J. Bartels, et al. (1997). "A peptide antibiotic from human skin." *Nature* 387(6636): 861.

Ihn, H. and K. Tamaki (2000). "Oncostatin M stimulates the growth of dermal fibroblasts via a mitogen-activated protein kinase-dependent pathway." *J Immunol* 165(4): 2149-55.

Jonak, C., G. Klosner, et al. (2002). "Subcorneal colocalization of the small heat shock protein, hsp27, with keratins and proteins of the cornified cell envelope." *Br J Dermatol* 147(1): 13-9.

Kira, M., S. Sano, et al. (2002). "STAT3 deficiency in keratinocytes leads to compromised cell migration through hyperphosphorylation of p130(cas)." *J Biol Chem* 277(15): 12931-6.

Koch, A. E., S. L. Kunkel, et al. (1994). "Epithelial neutrophil activating peptide-78: a novel chemotactic cytokine for neutrophils in arthritis." *J Clin Invest* 94(3): 1012-8.

Komine, M., L. S. Rao, et al. (2000). "Inflammatory versus proliferative processes in epidermis. Tumor necrosis factor alpha induces K6b keratin synthesis through a transcriptional complex containing NFkappa B and C/EBPbeta." *J Biol Chem* 275(41): 32077-88.

Lugering, N., T. Kucharzik, et al. (1997). "Importance of combined treatment with IL-10 and IL-4, but not IL-13, for inhibition of monocyte release of the Ca(2+)-binding protein MRP8/14." *Immunology* 91(1): 130-4.

Madsen, P., H. H. Rasmussen, et al. (1991). "Molecular cloning, occurrence, and expression of a novel partially secreted protein "psoriasin" that is highly up-regulated in psoriatic skin." *J Invest Dermatol* 97(4): 701-12.

Mehul, B., D. Bernard, et al. (2001). "Calmodulin-like skin protein: a new marker of keratinocyte differentiation." *J Invest Dermatol* 116(6): 905-9.

Mehul, B., D. Bernard, et al. (2000). "Identification and cloning of a new calmodulin-like protein from human epidermis." *J Biol Chem* 275(17): 12841-7.

Nagase, H. and J. F. Woessner, Jr. (1999). "Matrix metalloproteinases." *J Biol Chem* 274(31): 21491-4.

Navarro, J. M., J. Casatorres, et al. (1995). "Elements controlling the expression and induction of the skin hyperproliferation-associated keratin K6." *J Biol Chem* 270(36): 21362-7.

Nizet, V., T. Ohtake, et al. (2001). "Innate antimicrobial peptide protects the skin from invasive bacterial infection." *Nature* 414(6862): 454-7.

Nomura, I., E. Goleva, et al. (2003). "Cytokine milieu of atopic dermatitis, as compared to psoriasis, skin prevents induction of innate immune response genes." *J Immunol* 171(6): 3262-9.

Ong, P. Y., T. Ohtake, et al. (2002). "Endogenous antimicrobial peptides and skin infections in atopic dermatitis." *N Engl J Med* 347(15): 1151-60.

Paglia, D., S. Kondo, et al. (1996). "Leukaemia inhibitory factor is expressed by normal human keratinocytes in vitro and in vivo." *Br J Dermatol* 134(5): 817-23.

Paramio, J. M., M. L. Casanova, et al. (1999). "Modulation of cell proliferation by cytokeratins K10 and K16." *Mol Cell Biol* 19(4): 3086-94.

Pattyn, F., F. Speleman, et al. (2003). "RTPrimerDB: the real-time PCR primer and probe database." *Nucleic Acids Res* 31(1): 122-3.

Pfaffl, M. W. (2001). "A new mathematical model for relative quantification in real-time RT-PCR." *Nucleic Acids Res* 29(9): e45.

Pilcher, B. K., M. Wang, et al. (1999). "Role of matrix metalloproteinases and their inhibition in cutaneous wound healing and allergic contact hypersensitivity." *Ann N Y Acad Sci* 878: 12-24.

Rogers, M. S., T. Kobayashi, et al. (2001). "Human calmodulin-like protein is an epithelial-specific protein regulated during keratinocyte differentiation." *Exp Cell Res* 267(2): 216-24.

Rollman, O., U. B. Jensen, et al. (2003). "Platelet derived growth factor (PDGF) responsive epidermis formed from human keratinocytes transduced with the PDGF beta receptor gene." *J Invest Dermatol* 120(5): 742-9.

Rosdy, M., B. Bertino, et al. (1997). "Retinoic acid inhibits epidermal differentiation when applied topically on the stratum corneum of epidermis formed in vitro by human keratinocytes grown on defined medium." *In Vitro Toxicology* 10(1): 39-47.

Roth, J., T. Vogl, et al. (2003). "Phagocyte-specific S100 proteins: a novel group of proinflammatory molecules." *Trends Immunol* 24(4): 155-8.

Ryckman, C., K. Vandal, et al. (2003). "Proinflammatory activities of S100: proteins S100A8, S100A9, and S100A8/A9 induce neutrophil chemotaxis and adhesion." *J Immunol* 170(6): 3233-42.

Sano, S., S. Itami, et al. (1999). "Keratinocyte-specific ablation of Stat3 exhibits impaired skin remodeling, but does not affect skin morphogenesis." *Embo J* 18(17): 4657-68.

Sugawara, T., R. M. Gallucci, et al. (2001). "Regulation and role of interleukin 6 in wounded human epithelial keratinocytes." *Cytokine* 15(6): 328-36.

Taga, T. and T. Kishimoto (1997). "Gp130 and the interleukin-6 family of cytokines." *Annu Rev Immunol* 15: 797-819.

Thorey, I. S., J. Roth, et al. (2001). "The Ca2+-binding proteins S100A8 and S100A9 are encoded by novel injury-regulated genes." *J Biol Chem* 276(38): 35818-25.

Vandesompele, J., K. De Preter, et al. (2002). "Accurate normalization of real-time quantitative RT-PCR data by geometric averaging of multiple internal control genes." *Genome Biol* 3(7): RESEARCH0034.

Wagener, F. A., H. E. van Beurden, et al. (2003). "The heme-heme oxygenase system: a molecular switch in wound healing." *Blood* 102(2): 521-8.

Wahl, A. F. and P. M. Wallace (2001). "Oncostatin M in the anti-inflammatory response." *Ann Rheum Dis* 60 Suppl 3: iii75-80.

Watson, P. H., E. R. Leygue, et al. (1998). "Psoriasin (S100A7)." *Int J Biochem Cell Biol* 30(5): 567-71.

The invention claimed is:

1. A method for promoting epidermal healing by promoting keratinocytes migration, comprising a step of administering a composition to a patient in need thereof, wherein said composition comprises a combination of oncostatin M (OSM), IL-17, and TNFα.

2. The method according to claim 1, wherein said composition increases in vitro the thickness of reconstituted human epidermis.

3. The method according to claim 1, further comprising the step of topically applying the composition to chaps on hands, lips, face or body to promote healing.

4. The method according to claim 1, further comprising the step of topically applying the composition to stretch marks to promote healing.

5. The method according to claim 1, further comprising the step of topically applying the composition to scars to promote healing.

* * * * *